United States Patent
Liu et al.

(10) Patent No.: US 11,065,428 B2
(45) Date of Patent: Jul. 20, 2021

(54) MICRONEEDLE ARRAY WITH ACTIVE INGREDIENT

(71) Applicant: Allergan, Inc., Irvine, CA (US)

(72) Inventors: Futian Liu, Lake Forest, CA (US); Xiaojie Yu, Orange, CA (US); Lance E. Steward, Irvine, CA (US); Guang Wei Lu, Irvine, CA (US); Patrick M. Hughes, Aliso Viejo, CA (US); Sheshadri Neervannan, Irvine, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 15/932,365

(22) Filed: Feb. 16, 2018

(65) Prior Publication Data

US 2018/0236215 A1    Aug. 23, 2018

Related U.S. Application Data

(60) Provisional application No. 62/460,261, filed on Feb. 17, 2017.

(51) Int. Cl.
*A61M 37/00* (2006.01)
*A61K 38/48* (2006.01)
(Continued)

(52) U.S. Cl.
CPC ....... *A61M 37/0015* (2013.01); *A61K 9/0021* (2013.01); *A61K 38/4893* (2013.01);
(Continued)

(58) Field of Classification Search
CPC ...... A61M 37/0015; A61M 2037/0023; A61M 2037/0061; A61M 2037/0053;
(Continued)

(56) References Cited

U.S. PATENT DOCUMENTS

| 5,093,198 A | 3/1992 | Speaker et al. |
| 5,586,466 A | 12/1996 | Feigner et al. |

(Continued)

FOREIGN PATENT DOCUMENTS

| CA | 2594291 | 7/2006 |
| CA | 2686093 | 10/2008 |

(Continued)

OTHER PUBLICATIONS

Bariya et al., Microneedles: an emerging transdermal drug delivery system, Journal of Pharmacy and Pharmacology, 2011, pp. 11-29.

(Continued)

*Primary Examiner* — Robert A Wax
*Assistant Examiner* — Quanglong N Truong
(74) *Attorney, Agent, or Firm* — Nathan S. Smith; Kalpesh V. Upadhye; Morgan, Lewis & Bockius LLP

(57) ABSTRACT

Microneedle arrays for introducing an active ingredient through a skin surface of a subject can include a base layer, a plurality of microneedles projecting from the base layer, and an active ingredient. Each of the microneedles comprises an elongate body having a proximal portion and a distal portion, in which the proximal portion is attached to the base layer. Each of the microneedles comprises at least one dissolvable polymer. The active ingredient is incorporated in the elongate body, and the active ingredient is present only in the distal portion and at least internally in the distal portion.

26 Claims, 7 Drawing Sheets

(51) Int. Cl.
    *A61K 47/36*     (2006.01)
    *A61P 17/06*     (2006.01)
    *A61P 29/00*     (2006.01)
    *A61K 9/00*     (2006.01)
    *A61K 47/42*     (2017.01)
    *B29C 33/42*     (2006.01)

(52) U.S. Cl.
    CPC .............. *A61K 47/36* (2013.01); *A61K 47/42* (2013.01); *A61P 17/06* (2018.01); *A61P 29/00* (2018.01); *A61M 2037/0023* (2013.01); *A61M 2037/0053* (2013.01); *A61M 2037/0061* (2013.01); *B29C 33/42* (2013.01)

(58) Field of Classification Search
    CPC ...... A61K 47/42; A61K 9/0021; A61K 47/36; A61K 38/4893; A61P 29/00; A61P 17/06; B29C 33/42
    See application file for complete search history.

(56) References Cited

U.S. PATENT DOCUMENTS

| | | |
|---|---|---|
| 6,334,856 B1 | 1/2002 | Allen et al. |
| 6,440,096 B1 | 8/2002 | Lastovich |
| 6,503,231 B1 | 1/2003 | Prausnitz et al. |
| 6,537,264 B1 | 3/2003 | Cormier et al. |
| 6,565,532 B1 | 5/2003 | Yuzhakov et al. |
| 6,611,707 B1 | 8/2003 | Prausnitz et al. |
| 6,623,457 B1 | 9/2003 | Rosenberg |
| 6,689,100 B2 | 2/2004 | Connelly et al. |
| 6,743,211 B1 | 6/2004 | Prausnitz et al. |
| 6,946,501 B2 | 9/2005 | Kovachar |
| 7,226,439 B2 | 6/2007 | Prausnitz et al. |
| 7,416,541 B2 | 8/2008 | Yuzhakov et al. |
| 8,366,677 B2 | 2/2013 | Kaspar et al. |
| 8,476,243 B2 | 7/2013 | Kaspar et al. |
| 8,530,436 B2 | 9/2013 | Kaspar |
| 8,545,741 B2 | 10/2013 | Jung et al. |
| 9,987,361 B1 | 6/2018 | Suzuki |
| 10,231,879 B2 | 3/2019 | Kim et al. |
| 2002/0082543 A1* | 6/2002 | Park ........................ A61N 1/30 604/21 |
| 2002/0111600 A1 | 8/2002 | Cormier et al. |
| 2002/0138049 A1 | 9/2002 | Allen et al. |
| 2003/0069548 A1 | 4/2003 | Connelly et al. |
| 2003/0167556 A1 | 9/2003 | Kelley |
| 2004/0009180 A1 | 1/2004 | Donovan |
| 2004/0049150 A1 | 3/2004 | Dalton et al. |
| 2005/0065463 A1 | 3/2005 | Tobinaga et al. |
| 2005/0197308 A1 | 9/2005 | Dalton et al. |
| 2005/0209565 A1 | 9/2005 | Yuzhakov et al. |
| 2005/0261632 A1 | 11/2005 | Xu |
| 2006/0057165 A1 | 3/2006 | Dimitrakoudis et al. |
| 2006/0100584 A1 | 5/2006 | Olejnik et al. |
| 2006/0127465 A1 | 6/2006 | Maeonsono et al. |
| 2007/0009587 A1 | 1/2007 | Daddona |
| 2007/0049901 A1 | 3/2007 | Wu et al. |
| 2007/0060867 A1 | 3/2007 | Xu |
| 2008/0009811 A1 | 1/2008 | Cantor |
| 2008/0125743 A1 | 5/2008 | Yuzhakov |
| 2008/0138420 A1 | 6/2008 | Speaker |
| 2008/0269666 A1 | 10/2008 | Wang et al. |
| 2008/0269685 A1 | 10/2008 | Singh et al. |
| 2009/0035446 A1* | 2/2009 | Kwon .................... A61K 9/0021 427/2.1 |
| 2009/0043279 A1 | 2/2009 | Kaspar et al. |
| 2009/0099502 A1 | 4/2009 | Tokumoto et al. |
| 2009/0131905 A1 | 5/2009 | Allen et al. |
| 2009/0182306 A1* | 7/2009 | Lee .................... A61M 37/0015 604/506 |
| 2010/0196445 A1 | 8/2010 | David |
| 2010/0221314 A1 | 9/2010 | Matsudo et al. |
| 2010/0228203 A1 | 9/2010 | Quan et al. |
| 2010/0280457 A1 | 11/2010 | Tokumoto et al. |
| 2011/0028905 A1 | 2/2011 | Takada |
| 2011/0098651 A1 | 4/2011 | Falo, Jr. et al. |
| 2011/0121486 A1 | 5/2011 | Oh et al. |
| 2011/0152792 A1 | 6/2011 | Takada |
| 2011/0177139 A1 | 7/2011 | Jung et al. |
| 2011/0177297 A1 | 7/2011 | Jung et al. |
| 2011/0190688 A1 | 8/2011 | Tagliaferri et al. |
| 2011/0195124 A1 | 8/2011 | Jin |
| 2011/0270221 A1 | 11/2011 | Ross |
| 2012/0027810 A1 | 2/2012 | Chen et al. |
| 2012/0029434 A1 | 2/2012 | Kobayashi |
| 2012/0150023 A1 | 6/2012 | Kaspar et al. |
| 2012/0193840 A1 | 8/2012 | Kwon |
| 2012/0220981 A1 | 8/2012 | Soo et al. |
| 2012/0283695 A1 | 11/2012 | Chen et al. |
| 2013/0012882 A1 | 1/2013 | Quan et al. |
| 2013/0072902 A1 | 3/2013 | Takada et al. |
| 2013/0078874 A1 | 3/2013 | Tokumoto et al. |
| 2013/0096532 A1 | 4/2013 | Ozel et al. |
| 2014/0142492 A1 | 5/2014 | Jung et al. |
| 2014/0180201 A1* | 6/2014 | Ding .................. A61M 37/0015 604/46 |
| 2014/0257189 A1* | 9/2014 | Quan .................... A61K 9/0021 604/173 |
| 2014/0272101 A1 | 9/2014 | Chen et al. |
| 2014/0276362 A1 | 9/2014 | Alvarez |
| 2014/0276378 A1 | 9/2014 | Chen et al. |
| 2014/0315942 A1 | 10/2014 | Kaspar et al. |
| 2015/0126923 A1* | 5/2015 | Falo, Jr. ............... A61K 9/0021 604/46 |
| 2015/0196359 A1 | 7/2015 | Paithankar |
| 2015/0209563 A1 | 7/2015 | Amir |
| 2015/0238527 A1 | 8/2015 | Chang |
| 2015/0297688 A1 | 10/2015 | Borodic |
| 2016/0001053 A1* | 1/2016 | Quan .................. A61M 37/0015 604/46 |
| 2016/0015952 A1* | 1/2016 | Omachi ............... A61K 9/0021 604/46 |
| 2016/0158511 A1* | 6/2016 | Jin ....................... A61K 9/0021 604/173 |
| 2016/0184279 A1 | 6/2016 | Kaspar et al. |
| 2017/0157380 A1 | 6/2017 | Ross |
| 2017/0190098 A1 | 7/2017 | Kim et al. |
| 2017/0209553 A1 | 7/2017 | Kaspar et al. |
| 2018/0207415 A1 | 7/2018 | Kim et al. |
| 2018/0345627 A1 | 12/2018 | Kaspar et al. |

FOREIGN PATENT DOCUMENTS

| | | |
|---|---|---|
| CA | 2698632 | 12/2010 |
| CN | 105854172 | 8/2016 |
| EP | 1632263 | 3/2008 |
| EP | 2213284 | 8/2010 |
| EP | 2653186 | 10/2013 |
| EP | 3144030 | 3/2017 |
| JP | 2003-238347 | 8/2003 |
| JP | 2005-272398 | 10/2005 |
| JP | 2009-201956 | 9/2009 |
| JP | 2009-254756 | 11/2009 |
| JP | 2010-082401 | 4/2010 |
| JP | 2011-167486 | 9/2011 |
| JP | 2011-224332 | 11/2011 |
| JP | 2012-025723 | 2/2012 |
| JP | 2012-031177 | 2/2012 |
| JP | 2012-041329 | 3/2012 |
| JP | 2013-009960 | 1/2013 |
| JP | 2013-032324 | 2/2013 |
| JP | 2013-052202 | 3/2013 |
| JP | 2013-075165 | 4/2013 |
| JP | 2016-083085 | 5/2016 |
| JP | 2016-512754 | 5/2016 |
| JP | 2016-518868 | 6/2016 |
| KR | 10-2007-0018410 | 2/2007 |
| KR | 20110116110 | 10/2011 |
| KR | 101285085 | 7/2013 |
| KR | 101386442 | 4/2014 |
| KR | 101663744 | 10/2016 |

(56) References Cited

FOREIGN PATENT DOCUMENTS

| | | |
|---|---|---|
| KR | 101684594 | 12/2016 |
| KR | 101684595 | 12/2016 |
| KR | 20170000423 U | 2/2017 |
| KR | 101738671 | 4/2017 |
| KR | 20170067637 | 6/2017 |
| KR | 20170080414 | 7/2017 |
| KR | 20170131283 | 12/2017 |
| KR | 101873827 | 7/2018 |
| KR | 101877273 | 7/2018 |
| KR | 20190085643 | 7/2019 |
| WO | WO 99/64580 | 12/1999 |
| WO | WO 00/44438 | 8/2000 |
| WO | WO 02/064193 | 8/2002 |
| WO | WO 2006/018642 | 2/2006 |
| WO | WO 2006/077742 | 7/2006 |
| WO | WO 2006/131931 | 12/2006 |
| WO | WO 2008/010681 | 1/2008 |
| WO | WO 2008/130587 | 10/2008 |
| WO | WO 2008/139786 | 11/2008 |
| WO | WO 2009/021048 | 2/2009 |
| WO | WO 2009/066763 | 5/2009 |
| WO | WO 2009/94394 | 7/2009 |
| WO | WO 2009154411 | 12/2009 |
| WO | WO 2010/056922 | 5/2010 |
| WO | WO 2010/078323 | 7/2010 |
| WO | WO 2010039006 | 8/2010 |
| WO | WO 2010039007 | 8/2010 |
| WO | WO 2010147303 | 12/2010 |
| WO | WO 2011/044367 | 4/2011 |
| WO | WO 2011/115272 | 9/2011 |
| WO | WO 2012/023044 | 2/2012 |
| WO | WO 2012081933 | 6/2012 |
| WO | WO 2012/115207 | 8/2012 |
| WO | WO 2012/122162 | 9/2012 |
| WO | WO 2012/122163 | 9/2012 |
| WO | WO 2012/128363 | 9/2012 |
| WO | WO 2012/153266 | 11/2012 |
| WO | WO 2013015563 | 1/2013 |
| WO | WO 2013/57819 | 4/2013 |
| WO | WO 2013/096206 | 6/2013 |
| WO | WO-2016155891 A1 * | 10/2016 ........... A61K 31/593 |
| WO | WO 2017061700 | 4/2017 |
| WO | WO 2017061701 | 4/2017 |
| WO | WO 2017115973 | 7/2017 |
| WO | WO 2017200213 | 11/2017 |
| WO | WO 2017200214 | 11/2017 |
| WO | WO 2018030639 | 2/2018 |
| WO | WO 2018052181 | 3/2018 |
| WO | WO 2018212592 | 11/2018 |
| WO | WO 2019050109 | 3/2019 |

OTHER PUBLICATIONS

Cormier et al., "Transdermal delivery of desmopressin using a coated microneedle array patch system," Journal of Controlled Release, 2004, vol. 97, pp. 503-511.

Donnelly et al., "Microneedle-based drug delivery systems: Microfabrication, drug delivery and safety," Drug Delivery, 2010, 17(4), pp. 187-207.

Gonzalez-Gonzalez et al.; Silencing of Reporter Gene Expression in Skin Using siRNAs Delivered by a Soluble Protrusion Array Device(PAD); Molecular Therapy; Sep. 2010; pp. 167-1674; vol. 18.

Lee et al, "Drawing lithography: three-dimensional fabrication of an ultrahigh-aspect-ratio microneedle," Advanced Materials, Jan. 2010, 22(4), pp. 483-486.

Li et al., "An optimized hollow microneedle for minimally invasive blood extraction," Biomedical Microdevices, Jul. 2012, 15(1), pp. 17-25.

Park et al., "Biodegradable polymer microneedles: Fabrication, mechanics and transdermal drug delivery," Journal of Controlled Release, vol. 104, No. 1, May 2005, pp. 51-66.

Prausnitz, "Microneedles for transdermal drug delivery," Advanced Drug Delivery Reviews. 2004, vol. 56, pp. 581-587.

Schmid, "Microneedles May Take the Ouch Out of Flue Shots, Researchers Developing Skin Patch for Influenza Vaccine," msnbc. com; http://www.msnbc.msn.com/id/38301183/from/toolbar; Jul. 18, 2010.

Shiseido News Release, The IFSCC Conference 2011, Development of self-dissolving microneedles consisting of hyaluronic acid as an anti-wrinkle treatment.

Wang et al., "Recent Advances in the design of polymeric microneedles for transdermal drug delivery and biosensing," Lab on a Chip, Mar. 2017, 17(8), pp. 1373-1387.

International Search Report and Written Opinion from PCT/US2018/000046, dated Jun. 7, 2018, 17 pages.

* cited by examiner

MICRONEEDLE ARRAY WITH ACTIVE INGREDIENT

CROSS-REFERENCE TO RELATED APPLICATIONS

This application claims the benefit of and priority to U.S. Provisional Application No. 62/460,261, filed Feb. 17, 2017, the entirety of which is incorporated herein by reference.

BACKGROUND

Field

The present disclosure relates generally to microneedle arrays and methods for producing and using microneedle arrays, and, more particularly, to microneedle arrays and associated methods in which an active ingredient is localized at a distal end of each microneedle.

Background

Drug delivery into or through the skin can be limited due to the inability of many drugs to penetrate the stratum corneum at therapeutically relevant rates during topical delivery. One approach that has been taken to improve drug permeability through the skin is to reversibly create a plurality of apertures large enough for drug molecules to pass through. Several techniques have been employed to this end including, for example, chemical permeation enhancement, iontophoresis, electroporation, ultrasonic pressure wave generation, and radiofrequency and/or heat ablation. These approaches can be problematic in some instances, most commonly due to the small aperture size produced. Larger drug molecules, such as biological entities, for example, are frequently too large to traverse the apertures created using these techniques. Because of their large size, biological entities are often administered by hypodermic injection, which can be painful for a subject and undesirable for treating certain skin surface areas in some instances.

An alternative approach for creating apertures in the skin utilizes microneedle arrays. Upon application of a microneedle array to a skin surface of a subject, multiple skin penetrations occur to allow drug molecules to pass through. Microneedle-created apertures are dictated by the cross-sectional size of the individual microneedles, which are typically many microns in width. As such, microneedle-created apertures can allow larger drug molecules such as antigens, antibodies and toxins to be introduced through the skin in order to perform a therapeutic function. Because of their small size and limited penetration depth, microneedle arrays do not generally cause significant pain for a subject, unlike hypodermic injections.

Microneedle arrays can be utilized in a number of ways to deliver drug molecules through the skin. In a "poke and patch" approach, a microneedle array is applied to the skin and then removed to create apertures, and a drug or drug patch is then applied topically over the created apertures. Fast healing of the apertures can limit the effectiveness of this approach. In a "coat and poke" approach, drug-coated microneedles are used both to create apertures and to deliver drug molecules through the skin. Limited and non-uniform coating of drug molecules onto the microneedles can be problematic in this approach. In a "poke and flow" approach, hollow microneedles are used to penetrate the skin, and the microneedles are then left in place to serve as a conduit for delivering a liquid drug through the skin.

SUMMARY

The present application discloses microneedle arrays, and in some embodiments, microneedle arrays that can be used for "poke and release" drug delivery applications, where degradable microneedles loaded with drug molecules are used to penetrate the skin, and after a length of time, the drug-loaded microneedles disengage from their substrate and are retained in the skin. In accordance with some embodiments, drug molecules or other active ingredients can be utilized more efficiently in this "poke and release" delivery motif through utilizing aspects of the disclosure herein than in conventional microneedle arrays intended for "poke and patch," "coat and poke," or "poke and flow" drug delivery applications.

Some embodiments of the microneedle arrays disclosed herein incorporate an active ingredient in a manner such that essentially the entirety of the active ingredient carried by the array is deliverable to a subject and higher active ingredient loadings are achievable than in conventional microneedle arrays intended for "poke and patch," "coat and poke," or "poke and flow" drug delivery applications. Further, some embodiments of the microneedle arrays discussed herein can be utilized in treating a variety of conditions and can be particularly effective for delivering biological entities, such as toxins, to a subject.

In accordance with some embodiments disclosed herein, a microneedle array can be provided that includes an active ingredient incorporated at least internally within each microneedle and only in the distal portion of each microneedle with respect to the base layer from which the microneedles project. For example, according to embodiments, the base layer and at least a portion of the elongate body defining each microneedle lacks an active ingredient. The active ingredient can be disposed uniformly in the distal portion of each microneedle or in a concentration gradient in the distal portion of each microneedle. For example, a concentration gradient of the active ingredient can be provided via layers of different concentrations, either increasing or decreasing concentrations or both increasing and decreasing concentrations, toward the distal portion of each microneedle. A proximal portion of each microneedle attached to the base layer of the microneedle arrays lacks the active ingredient. As such, upon separation of the microneedles from the base layer following application to a skin surface of a subject, none of the active ingredient is lost to waste when the base layer is subsequently removed from the skin surface. Although each microneedle is relatively small and holds only a small amount of active ingredient, therapeutically effective amounts of the active ingredient can be delivered upon collective dissolution or degradation of the microneedles.

In some embodiments, the microneedles are formed from a dissolvable polymer which can dissolve or degrade under physiological conditions. In some embodiments, the dissolvable polymer comprises a polymeric material that dissolves in an aqueous medium. In some embodiments, the aqueous medium is phosphate buffered saline (PBS). In some embodiments, the PBS has a pH in the range of about 4.0 to about 10.0, about 4.5 to about 9.5, about 5 to about 8, about 5.5 to about 7.5, about 6 to about 8, about 6.5 to about 7.5, about 6.8 to about 7.8, or about 7.0 to about 7.8. In some embodiments, the dissolvable polymer comprises a polymeric material that dissolves in pH 7.4 PBS. In some embodiments, the polymeric material dissolves in pH 7.4 PBS at a temperature in the range of about 10° C. to about 50° C., about 15° C. to about 45° C., about 20° C. to about 40° C., about 25° C. to about 45° C., about 30° C. to about 40° C., about 35° C. to about 45° C., or about 35° C. to about 40° C.

In order to fabricate some embodiments of the microneedle arrays discussed above, a microneedle mold having a plurality of elongate wells can be contacted with a first fluid containing a first dissolvable polymer and an active ingredient, such that the elongate wells are only partially filled, specifically in their lower portions, thereby leaving an upper portion of each of the elongate wells unfilled. After partially filling the lower portions of each of the elongate wells with the first fluid, a second fluid containing a second dissolvable polymer but lacking the active ingredient of the first fluid or any other active ingredients can be applied to the mold to complete fabrication of the base layer and the elongate body of each microneedle. In some embodiments, mixing of the first fluid and the second fluid can be precluded due to viscosity effects, thereby localizing the active ingredient in the distal portion of each of the microneedles. In some embodiments, the first dissolvable polymer and the second dissolvable polymer can be the same, such that the microneedle arrays are compositionally homogenous, except for the distal portions of the microneedles, in which the active ingredient is incorporated. In other embodiments, the first dissolvable polymer and the second dissolvable polymer can be different. Further, in some embodiments, a gradient distribution of the active ingredient can be incorporated in the microneedles by sequentially depositing aliquots of the first dissolvable polymer having differing concentrations of the active ingredient and then overfilling the upper portions of the elongate wells with the second dissolvable polymer.

Some embodiments disclosed herein can be configured such that the active ingredient is disposed only in the distal portion of the elongate body defining each of the microneedles, and the active ingredient is incorporated at least internally within the elongate body in the distal portion, specifically within a matrix defined by the dissolvable polymer. Incorporation of the active ingredient internally within the microneedles provides significant advantages in many respects over tip-coated microneedles used in conventional "coat and poke" drug delivery approach.

Accordingly, some embodiments of a microneedle array can include a base layer and a plurality of microneedles projecting from the base layer. Each of the microneedles comprises an elongate body having a proximal portion and a distal portion, and the proximal portion is attached to the base layer. The microneedles and the base layer can be dissolvable. For example, the microneedles and the base layer can comprise at least one dissolvable polymer. An active ingredient can be incorporated in the elongate body of each microneedle, with the active ingredient being present only in the distal portion of each elongate body and at least internally within the distal portion. The active ingredient can be disposed uniformly in the distal portion or in a gradient fashion in the distal portion.

In some embodiments, the active ingredient present in the microneedle arrays comprises drug molecules or biomolecules (i.e., biological entities). In some embodiments, the active ingredient comprises an antigen, antibody, or toxin. In still some embodiments, the active ingredient is a neurotoxin such as a botulinum toxin, for example. Botulinum toxin of types A, B, C, D and/or E can be present in the microneedle arrays. In some embodiments, the botulinum toxin is selected from the group consisting of Botulinum toxin serotype A (BoNT/A), Botulinum toxin serotype B (BoNT/B), Botulinum toxin serotype C1 (BoNT/C1), Botulinum toxin serotype D (BoNT/D), Botulinum toxin serotype E (BoNT/E), Botulinum toxin serotype F (BoNT/F), Botulinum toxin serotype G (BoNT/G), Botulinum toxin serotype H (BoNT/H), Botulinum toxin serotype X (BoNT/X), Botulinum toxin serotype J (BoNT/J), and mosaic Botulinum toxins and/or variants thereof. Examples of mosaic toxins include BoNT/DC, BoNT/CD, and BoNT/FA. In some embodiments, the botulinum toxin can be a sub-type of any of the foregoing botulinum toxins.

In some embodiments, the at least one dissolvable polymer of each microneedle can comprise a first dissolvable polymer, where the distal portion and the proximal portion of each microneedle both comprise the first dissolvable polymer. In some embodiments, the base layer also comprises the first dissolvable polymer. In some embodiments, the base layer and the proximal portion both comprise the first dissolvable polymer and lack the active ingredient or any other active ingredients. In some embodiments, the base layer and the proximal portion can both consist of the first dissolvable polymer and lack the active ingredient, which can instead be incorporated in a matrix of the first dissolvable polymer in the distal portion of each elongate body.

In some embodiments, one or more microneedles of the array can comprise a plurality of dissolvable polymers, such as first and second dissolvable polymers. For example, the distal portion of each elongate body can comprise the first dissolvable polymer, and the proximal portion of each elongate body can comprise the second dissolvable polymer. The base layer can similarly comprise or consist of the second dissolvable polymer. In some embodiments, the first dissolvable polymer and/or the second dissolvable polymer can comprise a plurality of dissolvable polymers. In some embodiments, the second dissolvable polymer can be subject to dissolution faster than the first dissolvable polymer. A faster-degrading second dissolvable polymer can facilitate release of the microneedles from the base layer. Differing dissolvable polymers can also facilitate tailoring of the mechanical properties of the microneedles, for example.

In some embodiments, the at least one dissolvable polymer comprises hyaluronic acid, crosslinked hyaluronic acid, hydrophobically modified hyaluronic acid, or any combination thereof.

In some embodiments, the at least one dissolvable polymer comprises at least one of a glycosaminoglycan, a polysaccharide, collagen, elastin, fibroin, starch, glucomannan, hyaluronic acid, crosslinked hyaluronic acid, hydrophobically modified hyaluronic acid, or any combination thereof.

Some embodiments of methods for forming the microneedle arrays are also disclosed herein. In some embodiments, a microneedle array mold can be provided that comprises a plurality of elongate wells having a lower portion and an upper portion, and filling the lower portion of each of the elongate wells with a first fluid comprising a first dissolvable polymer and an active ingredient, such that each of the elongate wells is only partially filled to leave the upper portion of each of the elongate wells unfilled. After filling the lower portion of each of the elongate wells, the unfilled upper portions of each of the elongate wells can be overfilling with a second fluid, which comprises a second dissolvable polymer and lacks the active ingredient. Thereafter, the mold can be heated or the first and second fluids can be dried or evaporated at room temperature to form a microneedle array comprising a base layer having a plurality of microneedles projecting therefrom. Furthermore, the microneedle array can be separated from the microneedle array mold. Drying or evaporating the first and second fluids at room temperature can be desirable when sensitive active ingredients are incorporated in the first fluid, such as proteins or other biomolecules.

Depending on the nature of the dissolvable polymers used, the first fluid and/or the second fluid can be rather viscous. Accordingly, in some embodiments, a casting process can be employed to promote fluid dispensation into a desired location within the mold. The casting process can aid dispensation of the first fluid into the lower portion or bottom of each elongate well and promote formation of the resulting microneedles.

In some embodiments, filling the lower portion of each of the elongate wells can comprise depositing, moving, or casting the first fluid into the lower portion of each of the elongate wells. Likewise, overfilling the upper portion of each of the elongate wells can comprise depositing, moving, or casting the second fluid. In some embodiments, the second fluid can be cast above the first fluid into the mold and/or within each of the elongate wells. The second fluid can be applied directly onto the first fluid, and the second fluid, in turn, can convey aid in depositing, moving, or casting the first fluid within or deeper into the lower portion of each of the elongate wells.

In some embodiments, at least a portion of the second fluid is disposed in an overfilled or base portion of the mold, such as a portion of the mold that is in fluid contact with or interconnects each of the elongate wells. In some embodiments, at least a portion of the overfilled second fluid disposed in the overfilled portion of the mold can define or form the base layer of the microneedle array.

Some embodiments of methods for treating a subject using a microneedle array are also disclosed herein. The methods can involve "poke and release" delivery of an active ingredient through a skin surface of a subject. More specifically, such methods comprise providing a microneedle array, and applying the microneedle array to a skin surface of a subject to embed the plurality of microneedles in the skin surface. The microneedle arrays comprise a base layer, a plurality of microneedles projecting from the base layer, and an active ingredient. Each of the microneedles can comprise an elongate body having a proximal portion and a distal portion, and the proximal portion is attached to the base layer. The microneedles and the base layer comprise at least one dissolvable polymer. An active ingredient is incorporated in the elongate body of each microneedle, with the active ingredient being present only in the distal portion of each elongate body and at least internally within the distal portion.

Upon becoming embedded in the skin surface of the subject, the at least one dissolvable polymer can dissolve or degrade over time under physiological conditions to release the active ingredient to the subject.

After the at least one dissolvable polymer dissolves or degrades, thereby releasing the microneedles from the base layer, the base layer can be removed from the skin surface of the subject. The microneedles and their incorporated active ingredient can thereafter remain within the subject to provide the desired effect.

Additional features and advantages of the subject technology will be set forth in the description below, and in part will be apparent from the description, or may be learned by practice of the subject technology. The advantages of the subject technology will be realized and attained by the structure particularly pointed out in the written description and embodiments hereof as well as the appended drawings.

It is to be understood that both the foregoing general description and the following detailed description are exemplary and explanatory and are intended to provide further explanation of the subject technology.

BRIEF DESCRIPTION OF THE DRAWINGS

Various features of illustrative embodiments of the present disclosure are described below with reference to the drawings. The illustrated embodiments are intended to illustrate, but not to limit, the present disclosure. The drawings contain the following figures FIG. 1 provides a side-view illustration of a microneedle array, according to some embodiments.

DETAILED DESCRIPTION

In the following detailed description, numerous specific details are set forth to provide a full understanding of the subject technology. It should be understood that the subject technology may be practiced without some of these specific details. In other instances, well-known structures and techniques have not been shown in detail so as not to obscure the subject technology. While the present description sets forth specific details of various embodiments, it will be appreciated that the description is illustrative only and should not be construed in any way as limiting. Furthermore, various applications of such embodiments and modifications thereto, which may occur to those who are skilled in the art, are also encompassed by the general concepts described herein.

The present disclosure addresses several challenges associated with conventional microneedle arrays intended for use in "poke and patch," "coat and poke," or "poke and flow" drug delivery applications. Specifically, some embodiments of the microneedle arrays can provide localized incorporation of an active ingredient within the microneedles, while also disposing the active ingredient at least internally within each microneedle. These features allow the active ingredient to be used more efficiently, while simultaneously averting the issues associated with microneedle coating approaches. Further advantageously, some embodiments of the microneedle arrays can avoid waste disposal issues for potentially hazardous active ingredients, such as neurotoxins.

Figure 1:
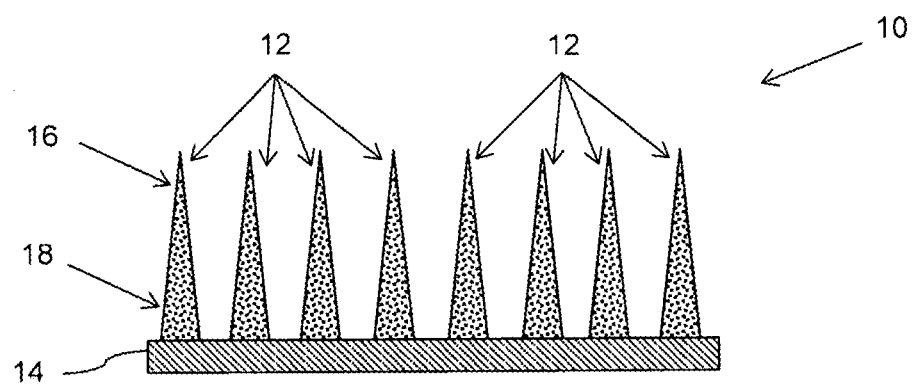
Figure 2:
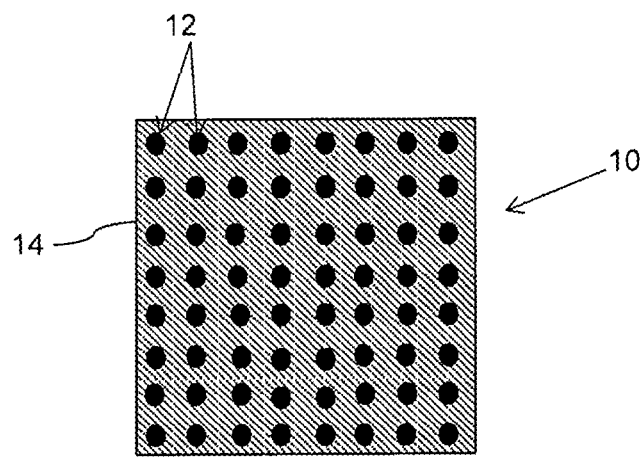
FIG. 2 provides a top-view illustration of a microneedle array, according to some embodiments.

In order to illustrate some aspects of the present disclosure, a microneedle array consistent with some embodiments will now be described in further detail. FIG. 1 provides a side-view illustration of a microneedle array 10, which contains a plurality of microneedles 12 projecting from a base layer 14. FIG. 2 provides a corresponding top view schematic of the microneedle array 10. Although an 8×8 array has been depicted in FIG. 2, it is to be recognized that the array dimensionality can be modified to suit the requirements of a particular application. Furthermore, the array dimensionality need not necessarily have the same number of rows and columns, as depicted in FIG. 2. In general, the array 10 can comprise any combination of rows and columns that is suitable for a given intended application. Further, the microneedle arrays are not limited to a rectangular configuration, as depicted in FIG. 2. Other illustrative microneedle array shapes can include, for example, circular, ovoid, elliptical, crescent or even irregular shaped, whether in a planar or three-dimensional configuration. For example, some embodiments can be used to provide a contour that facilitates use in treatments for the face or other areas of the body.

Referring further to FIG. 1, each of the microneedles 12 comprises an elongate body that includes a distal portion 16 and a proximal portion 18. The proximal portion 18 is attached to or contiguous with the base layer 14, and the distal portion 16 is spaced apart from the base layer 14 via proximal portion 18. The relative lengths of the proximal portion 18 and the distal portion 16 can vary over a wide range, and the particular disposition shown in FIG. 1 should be considered illustrative and non-limiting.

According to some embodiments of the present disclosure, an active ingredient can be incorporated within the microneedles 12 only in the distal portion 16 of each of the microneedles. As such, in some embodiments, the active ingredient can be spaced apart from and not present in the base layer 14, and at least a portion of the elongate body can lack the active ingredient. The active ingredient can be disposed uniformly or in a gradient fashion in distal portion 16. For example, in some embodiments, the gradient distribution of the active ingredient can be created by sequentially depositing aliquots of differing active ingredient concentrations to form the microneedles 12.

In some embodiments, the disposition of the distal portion 16 and the proximal portion 18 defining the elongate body of each of the microneedles 12 can vary over a range of relative lengths. In general, the proximal portion 18 can comprise at least 1% to about 99% of the length of the elongate body defining each of the microneedles 12, and the balance of the length is defined by the distal portion 16. In some embodiments, the proximal portion 18 can comprise between about 1% to about 10% of the length of the elongate body defining each of the microneedles 12, or between about 10% to about 20% of the length of the elongate body, or between about 20% to about 30% of the length of the elongate body, or between about 30% to about 40% of the length of the elongate body, or between about 40% to about 50% of the length of the elongate body, or between about 50% to about 60% of the length of the elongate body, or between about 60% to about 70% of the length of the elongate body, or between about 70% to about 80% of the length of the elongate body, or between about 80% to about 90% of the length of the elongate body. In each case, the distal portion 16 fills out the balance of the overall length.

In some embodiments, each of the microneedles 12 can have a length ranging between about 25 microns and about 3000 microns. In some embodiments, each of the microneedles 12 can have a length ranging between about 25 microns and about 1000 microns. In some embodiments, all of the microneedles 12 can have substantially the same length. Microneedle lengths within the foregoing ranges can be effective for penetrating a skin surface of a subject and delivering an active ingredient to the dermis, as discussed further herein. Delivery of an active ingredient to the dermis can improve skin quality and treat a variety of conditions affecting the skin, both cosmetic and clinical.

In some embodiments, each of the microneedles 12 can have a conical or pyramidal geometry suitable for perforating the skin. The conical or pyramidal geometry has a pitch angle associated therewith, such that the microneedles 12 taper to a point or tip suitable for perforating the skin.

In some embodiments, the microneedles 12 can have a tip width ranging between about 1 microns to about 30 microns. In some embodiments, the microneedles 12 can have a tip width ranging between about 4 microns to about 25 microns. The foregoing microneedle widths can be measured at the distalmost end or point of the microneedle or with respect to the location where the proximal portion 18 projects from the base layer 14, given that the microneedles 12 taper to a point in some embodiments. Microneedle tip widths within the foregoing size ranges can generate apertures of suitable size in the skin to deliver active ingredients varying over a wide size range, including biomolecules.

As indicated above, the number, dimensionality, length, width and geometry of the microneedles 12 within the microneedle array 10 is not considered to be particularly limited. Similarly, in some embodiments, a density of the microneedles 12 within the microneedle array 10 can range between about 5 microneedles/cm$^2$ to about 1000 microneedles/cm$^2$ or more.

According to some embodiments of the present disclosure, the microneedles 12 and the base layer 14 can be formed from a dissolvable polymer, such that the microneedles 12 are contiguous with the base layer 14 and project therefrom. Thus, in some embodiments, there is no structural discontinuity between the microneedles 12 and the base layer 14. In some embodiments, the dissolvable polymer of the microneedles 12 blends into the dissolvable polymer of the base layer 14.

As indicated above, at least a portion of the length of the elongate bodies defining the microneedles 12 can lack the active ingredient, such that the active ingredient is also not present in the base layer 14. In some embodiments, the base layer 14 can optionally comprise the same and/or different dissolvable polymer(s) that are present in microneedles 12.

In some embodiments, the microneedles 12 can comprise a first dissolvable polymer, such that the proximal portion 18 and the distal portion 16 both comprise the first dissolvable polymer. In some embodiments, the active ingredient can be incorporated only within a matrix of the first dissolvable polymer within the distal portion 16. In some embodiments, the base layer 14 can also comprise the first dissolvable polymer. Alternately, the base layer 14 can comprise a second dissolvable polymer that differs from the first dissolvable polymer comprising the microneedles 12.

In some embodiments, the microneedles 12 and/or the base layer 14 can each comprise one, two, three, or more polymers or layers, which can comprise dissolvable polymers. For example, the microneedles 12 can comprise a first dissolvable polymer and a second dissolvable polymer, such that distal portion 16 comprises the first dissolvable polymer and the proximal portion 18 comprises the second dissolvable polymer. Accordingly, in such embodiments, the active ingredient can be incorporated in distal portion 16 within a matrix of the first dissolvable polymer; further, in some embodiments, there may not be substantially any active ingredient present in the second dissolvable polymer within the proximal portion 18. In some embodiments, the base layer 14 can comprise the first dissolvable polymer and/or the second dissolvable polymer. In some embodiments, the base layer 14 comprises only the second dissolvable polymer. Alternately, the base layer 14 can comprise a third dissolvable polymer that differs from the first dissolvable polymer and/or the second dissolvable polymer comprising microneedles 12. The particular combination of dissolvable polymers can be chosen to tailor the microneedle properties for a desired application, such as to provide a desired release profile, blending profile, and/or mechanical strength, for example. For example, a faster-degrading dissolvable polymer can be present in the proximal portion of the microneedles 12 to release the distal portion of the microneedles 12 from the base layer 14 to ensure that when the array 10 is removed, the active ingredient in the distal portion of the microneedles 12 remains in the patient.

Optionally, both the microneedles 12 and the base layer 14 comprise the same type of dissolvable polymer. By having the same dissolvable polymer present in both the microneedles 12 and the base layer 14, potential incompatibilities between dissolvable polymers having different properties can be averted. For example, by configuring the microneedle array 10 such that the microneedles 12 and the base layer 14 are formed from the same dissolvable polymer, premature release of microneedles 12 through delamination can be avoided or precluded. However, in some embodiments, different dissolvable polymers can be desirable and advantageously used for some applications, including some applications within the context of the present disclosure.

In some embodiments, the device may include a first region sized and/or shaped to cover a first portion of skin to be treated, and a second region adjacent and connected to the first region, the second region sized and/or shaped to cover a second portion of skin to be treated. In some embodiments, the first region includes first microneedles projecting from the substrate and having a first length, and the second region includes second microneedles projecting from the substrate and having a second length, different from the first length, projecting from the first region and second microneedles having a second height different from the first height, projecting from the second region. In some embodiments, the first length is at least about 1% greater in length than the second length.

For example, in some embodiments, the first length is at least about 5%, at least about 10%, at least about 20%, at least about 30%, at least about 40%, at least about 50%, at least about 60%, at least about 70%, at least about 80%, at least about 90%, at least about 100%, at least about 150%, at least about 200%, at least about 300%, at least about 500%, at least about 800%, or at least about 1000% greater in length than the second length. In some embodiments, the first microneedles may have a length that is at least about 10% to about 200% greater than the length of the second microneedles. For example, the first microneedles have a length that is about 30%, or about 40%, or about 50%, or about 60%, or about 70%, or about 80%, or about 90%, or about 100%, or about 110%, or about 120%, or about 130%, or about 140%, or about 150%, or about 160%, or about 170%, or about 180%, or about 190%, or about 200% or greater than the length of the second microneedles.

In some embodiments, the first array comprises microneedles having a first length and the second array comprises microneedles having a second length different from the first length. In other embodiments, the first array comprises microneedles having a first spacing and the second array comprises microneedles having a second spacing different from the first spacing.

In order for the microneedles 12 to penetrate the skin surface of a subject effectively, sufficient mechanical strength of the at least one dissolvable polymer is desirable. Due to their relatively good mechanical properties, suitable dissolvable polymers for utilization in some embodiments of the present disclosure include, for example, a glycosaminoglycan, a polysaccharide, collagen, elastin, fibroin, starch, glucomannan, hyaluronic acid, crosslinked hyaluronic acid, hydrophobically modified hyaluronic acid, or any combination thereof. Other types of dissolvable polymers can also be suitable and can optionally be used alone or in combination with the foregoing dissolvable polymers. Carboxymethylcellulose, carboxyethylcellulose, and polyvinylalcohol, for example, are other types of dissolvable polymers that can be utilized in the present disclosure. In particular embodiments, hyaluronic acid can be blended with any of the foregoing dissolvable polymers.

In some embodiments, the at least one dissolvable polymer can comprise hyaluronic acid, crosslinked hyaluronic acid, hydrophobically modified hyaluronic acid, or any combination thereof. Various properties of the hyaluronic acid, crosslinked hyaluronic acid, or hydrophobically modified hyaluronic acid can be modulated to adjust the release profile of the active ingredient from the microneedles 12 upon application of the microneedle array 10 to a skin surface of a subject. Other dissolvable polymers can also be blended with hyaluronic acid to further modulate these properties. In addition to their ability to incorporate a variety of active ingredients, hyaluronic acid and modified hyaluronic acids can convey their own beneficial properties to a subject's skin, according to some embodiments.

In some embodiments, the hyaluronic acid, crosslinked hyaluronic acid, or hydrophobically modified hyaluronic acid can have a molecular weight ranging between about 10 kDa and about 6000 kDa. In some embodiments, the at least one dissolvable polymer comprises hyaluronic acid, crosslinked hyaluronic acid, or hydrophobically modified hyaluronic acid having a molecular weight ranging between about 100 kDa and about 6000 kDa.

In some embodiments, crosslinked hyaluronic acid can have a storage modulus (G') of about 100 Pa to about 3000 Pa. Suitable crosslinking agents for forming crosslinked hyaluronic acid include, for example, epoxy crosslinking agents such as 1,4-butanediol diglycidyl ether (BDDE), divinyl sulfone (DVS), or molecules containing at least two amine groups. In some embodiments, crosslinked hyaluronic acid can be formed via a thiol-Michael addition reaction. For example, thiolated hyaluronic acid can be crosslinked with maleimide-, vinyl sulfone-, or (meth)acrylate-modified hyaluronic acid. Polymer crosslinking in the presence of the active ingredient results in a well-mixed first fluid for use in some embodiments disclosed herein.

In some embodiments, hydrophobically modified hyaluronic acid can include hyaluronic acid that has been functionalized with alkyl or acyl groups, particularly alkyl groups. Alkyl groups suitable for forming hydrophobically modified hyaluronic acid include, for example, ethyl, propyl, benzyl and octyl groups, which can be linear or branched.

In some embodiments, hydrophobically modified hyaluronic acid can be swollen in the presence of phosphate buffered saline (PBS) or dimethyl sulfoxide (DMSO). Other hyaluronic acid compounds can be swollen similarly for use in various embodiments.

Dissolvable polymers having sufficient mechanical strength for forming a microneedle array can produce very viscous fluids upon being disposed in or mixed with a solvent. The high fluid viscosity can result in difficult introduction to a microneedle array mold for forming the microneedle arrays of the present disclosure. Suitable methods for addressing excessive fluid viscosity when forming a microneedle array are discussed in more detail hereinbelow. As such, microneedle arrays of the present disclosure can incorporate a wide range of dissolvable polymers. In addition, the present disclosure is compatible with a range of active materials, illustrative examples of which are discussed hereinafter.

As used herein, the term "active ingredient" refers to any substance which has a therapeutically desired effect when administered to a subject through the skin. In some embodiments, the active ingredient in the microneedle array can differ from the dissolvable polymer(s) present in the microneedle arrays. In particular embodiments, active materials suitable for incorporation within the microneedle arrays of the present disclosure include antigens, antibodies, and toxins. Since the microneedle arrays of the present disclosure lack an active material in the base layer, potential biohazardous waste disposal issues can be avoided when incorporating these biological entities in the microneedle arrays of the present disclosure.

Neurotoxins, particularly a botulinum toxin, can be especially desirable for incorporation within some embodiments of the microneedle arrays disclosed herein. Any of botulinium toxin types A, B, C, D, E or any combination thereof can be incorporated within the microneedle arrays of the present disclosure. In some embodiments, the botulinum toxin is selected from the group consisting of Botulinum toxin serotype A (BoNT/A), Botulinum toxin serotype B (BoNT/B), Botulinum toxin serotype C1 (BoNT/C1), Botulinum toxin serotype D (BoNT/D), Botulinum toxin serotype E (BoNT/E), Botulinum toxin serotype F (BoNT/F), Botulinum toxin serotype G (BoNT/G), Botulinum toxin serotype H (BoNT/H), Botulinum toxin serotype X (BoNT/X), Botulinum toxin serotype J (BoNT/J), and mosaic Botulinum toxins and/or variants thereof. Examples of mosaic toxins include BoNT/DC, BoNT/CD, and BoNT/FA. In some embodiments, the botulinum toxin can be a sub-type of any of the foregoing botulinum toxins.

The amount of active ingredient integrated into the microneedle array can vary, and may depend on several factors including but not limited to the type of active ingredient, the intended area of application, the type of treatment that is being conducted, the dose to be delivered, and the efficiency of delivering the active ingredient to the host from the device. In some embodiments, the microneedle array can comprise from 0.001% to about 15%, about 0.001% to about 10%, about 0.001% to about 3%, about 0.001% to about 1%, about 0.001% to about 0.5%, or 0.001% to about 0.1% by weight of the entire microneedle array of an active ingredient.

In some embodiments, the active ingredient is present only a distal portion of each of the microneedles of the microneedle array. In such a configuration, the distal portion of each of the microneedles can comprise from 0.001% to about 15%, about 0.001% to about 10%, about 0.001% to about 3%, about 0.001% to about 1%, about 0.001% to about 0.5%, or 0.001% to about 0.1% by weight of the distal portion of an active ingredient.

In some embodiments, the microneedle array can be configured into a patch for delivery of the active ingredient. In some embodiments, the patch is configured to deliver an effective amount of the active ingredient.

The dosage delivery can be measured in Units (U) per square centimeter. In toxicology, units of a given toxin can be determined by the LD50 of the toxin, the dose required to kill half of a test population. In some embodiments, the patch is configured to deliver a toxin in the amount of about 0.01 to about 100 $U/cm^2$, about 0.05 to about 95 $U/cm^2$, about 0.10 to about 90 $U/cm^2$, about 0.20 to about 85 $U/cm^2$, about 0.25 to about 80 $U/cm^2$, about 0.50 to about 75 $U/cm^2$, about 0.75 to about 70 $U/cm^2$, about 1.0 to about 65 $U/cm^2$, about 2.0 to about 60 $U/cm^2$, about 3.0 to about 55 $U/cm^2$, about 4.0 to about 50 $U/cm^2$, about 5.0 to about 45 $U/cm^2$, about 5.0 to about 40 $U/cm^2$, about 5.0 to about 35 $U/cm^2$, about 5.0 to about 30 $U/cm^2$, about 5.0 to about 25 $U/cm^2$, about 0.01 to about 20 $U/cm^2$, about 0.01 to about 15 $U/cm^2$, about 0.01 to about 10 $U/cm^2$, about 0.01 to about 5 $U/cm^2$, about 0.10 to about 15 $U/cm^2$, about 0.10 to about 10 $U/cm^2$, about 0.05 to about 10 $U/cm^2$, about 0.01 to about 3.0 $U/cm^2$, about 0.10 to about 3.0 $U/cm^2$, or about 0.05 to about 3.0 $U/cm^2$.

In some embodiments, the active ingredient has a loading concentration that exceeds the intended delivery dose to compensate for inefficient delivery. For example, for a composition configured to deliver a dose of 0.1 $U/cm^2$ having a delivery efficiency (percent of total drug contained in composition that is delivered to the subject) of 0.1%, the loading concentration would be about 10 $U/cm^2$. In some embodiments, the loading concentration is in the range of about 0.01 to about 100,000 $U/cm^2$, about 0.10 to about 80,000 $U/cm^2$, about 0.50 to about 50,000 $U/cm^2$, about 1.0 to about 25,000 $U/cm^2$, about 2.0 to about 15,000 $U/cm^2$, about 0.10 to about 20,000 $U/cm^2$, about 0.10 to about 15,000 $U/cm^2$, about 0.10 to about 10,000 $U/cm^2$, about 0.10 to about 8,000 $U/cm^2$, about 0.10 to about 5,000 $U/cm^2$, about 0.10 to about 1,000 $U/cm^2$, about 5.0 to about 1,000 $U/cm^2$, about 5.0 to about 10,000 $U/cm^2$, about 10 to about 100,000 $U/cm^2$, about 10 to about 90,000 $U/cm^2$, about 10 to about 75,000 $U/cm^2$, about 10 to about 50,000 $U/cm^2$, about 10 to about 25,000 $U/cm^2$, about 10 to about 10,000 $U/cm^2$, about 10 to about 1,000 $U/cm^2$, about 10 to about 500 $U/cm^2$, about 10 to about 250 $U/cm^2$, about 10 to about 100 $U/cm^2$, or about 10 to about 50 $U/cm^2$.

Advantages of some embodiments of the microneedle arrays disclosed herein include increasing skin permeability for a variety of biological entities or other active ingredients, permitting slow therapeutic release to be realized while reducing complications from localized or systemic diffusion, providing a large treatment area relative to a single-site injection, and creating less pain for a subject compared to hypodermic administration of an active material. In some embodiments, the microneedle arrays can optionally contain hyaluronic acid with one or more excipients. Hyaluronic acid with adequate molecular weight (e.g., 150 kDa to 6000 kDa) serves as the base material for maintaining microneedle integrity, while excipients such as, for example, sucrose, maltose, polyethylene glycol, or low molecular weight polymers (e.g., hyaluronic acid having a molecular weight <100 kDa), which can dissolve quickly in the skin to promote better delivery of the active ingredient. In some embodiments, the excipient can be a low molecular weight hyaluronic acid having a molecular weight of about 5 kDa, about 10 kDa, about 15 kDa, about 20 kDa, about 25 kDa, about 30 kDa, about 35 kDa, about 40 kDa, about 45 kDa, about 50 kDa, about 55 kDa, about 60 kDa, about 65 kDa, about 70 kDa, about 75 kDa, about 80 kDa, about 85 kDa, about 90 kdA, or about 95 kDa.

Figure 3:
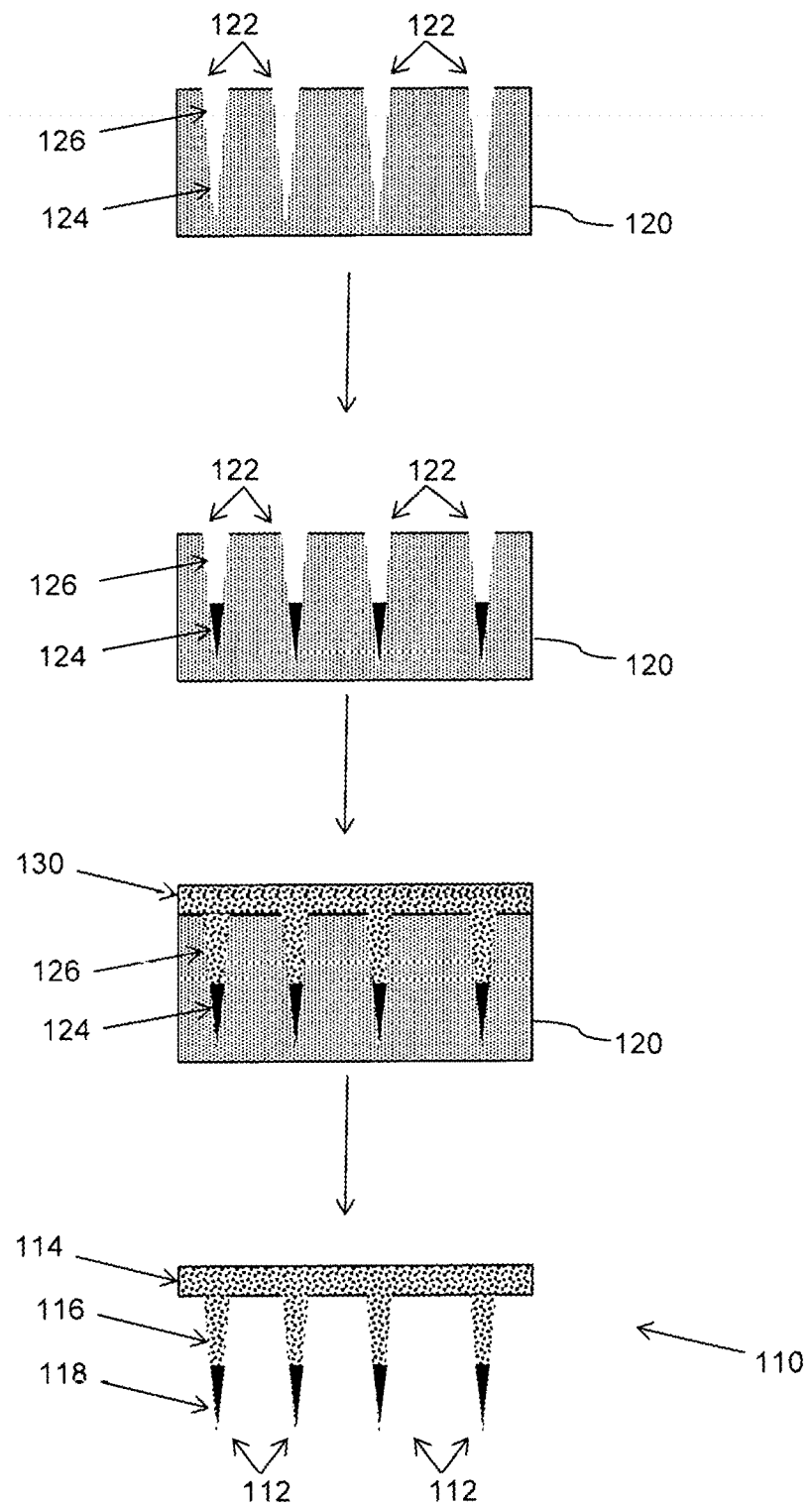
FIG. 3 shows an illustrative process schematic, as observed from a side view, through which a microneedle array is fabricated, according to some embodiments.

Facile methods are also described herein for fabricating the microneedle arrays discussed hereinabove. FIG. 3 shows an illustrative process, as observed from a side view, through which a microneedle array can be fabricated with an active ingredient disposed in only a distal portion of the microneedles. As shown in FIG. 3, methods for fabricating the microneedle array 110 first include providing the microneedle array mold 120 containing a plurality of elongate wells 122. Each of the elongate wells 122 can contain a lower portion 124 and an upper portion 126.

With continued reference to FIG. 3, a first fluid containing a first dissolvable polymer and an active ingredient is then prepared or provided. The first fluid is then used to partially fill each of the elongate wells 122. Specifically, the first fluid fills the lower portion 124 of each of the elongate wells 122, thereby leaving the upper portion 126 unfilled. A casting or deposition process can be utilized, as needed, to deposit the first fluid into the bottom of the elongate wells 122. Settling can take place during the casting process. If needed, a solvent can be driven off from the first fluid housed within the elongate wells 122 before proceeding further. In any case, the active ingredient remains incorporated throughout a matrix of the first dissolvable polymer within the lower portion 124 of each of the elongate wells 122. Suitable methods of casting polymers are described in U.S. Publication No. 2016/0279401, which is herein incorporated by reference in its entirety. Further, U.S. Publication No. 2016/0279401 also discusses additional features of microneedle arrays that can be combined with one or more features of the disclosure herein.

For example, any of the drug molecules or other active ingredients disclosed herein can be homogeneously embedded or incorporated into the entirety of the polymeric matrix of a microneedle array. The homogeneous incorporation can be found throughout the entirety of the microneedle array from the base of the array to the tip of each microneedle extending therefrom. By forming the microneedles with a drug or other active agent homogeneously incorporated into the polymeric matrix, the release rate of the drug or active agent can be carefully controlled. In addition, incorporation of the drug or active agent may provide the further benefit of uniformity that is not found in needles in which the drug or active agent is coated onto a surface. Furthermore, incorporation can prevent the loss of active agent due to detachment from the surface of the microneedles.

With continued reference to FIG. 3, a second fluid is prepared or provided, which comprises a second dissolvable polymer but lacks the active ingredient of the first fluid or any other active ingredient. In some embodiments, the second fluid can consist of or consist essentially of the second dissolvable polymer in admixture with a solvent. Depending on the intended outcome, the first dissolvable polymer and the second dissolvable polymer can be the same or different from one another. The second fluid is then used to fill the remainder of the elongate wells 122, specifically the upper portion 126 of each of the elongate wells 122.

In order to achieve connectivity between the microneedles 112 within the microneedle array 110, the elongate wells 122 can be overfilled with the second fluid. The overfilled second fluid can thereby coalesce into a single, continuous layer 130 above elongate wells 122 within the microneedle array mold 120. The second fluid can be settled through utilization of a second casting or deposition process, as needed, to deposit the second fluid deeper into elongate wells 122. The settling force can be further conveyed from the second fluid to the first fluid to result in further deposition or filling of the elongate wells 122 and/or densification of the microneedles 112. The continuous layer 130 can thereafter become a base layer 114 upon solidification, where the dissolvable polymer in the second fluid subsequently defines the base layer 114. Finally, after solidification, the base layer 114 and the remainder of the microneedle array 110 can be released or removed from the microneedle array mold 120.

Once the first fluid and the second fluid have been disposed within the microneedle array mold 120, the mold 120 and the microneedle array 110 can be heated to dry the fluids or drive off solvent to form the microneedle array 110, leaving behind the first and second dissolvable polymers and the active ingredient. Alternately, the first and second fluids can be evaporated or dried at room temperature to leave behind the first and second dissolvable polymers and the active ingredient in the form of microneedle array 110. After formation, the microneedle array 110 contains base layer 114 and a plurality of microneedles 112 projecting therefrom. Following release from the microneedle array mold 120, the microneedle array 110 is ready for further use.

Referring still to FIG. 3, and with further reference to FIG. 1, it can be seen that the microneedles 112 and the base layer 114 are contiguous with one another. For example, there a smooth interface can be present between the microneedles 112 and the base layer 114 with no structural discontinuities between the two. Specifically, the proximal portion 116 and the base layer 114 are contiguous with one another. In some embodiments, the proximal portion 116 and the base layer 114 are substantially the same compositionally. Both the proximal portion 116 and the base layer 114 can lack the active ingredient or other active ingredients, as discussed above in regard to FIG. 1. The distal portion 118 of the microneedles 112, in contrast, can contain the active ingredient incorporated throughout a matrix of the dissolvable polymer. Since the dissolvable polymer and the active ingredient are admixed in the first fluid prior to forming the microneedles 112, the active ingredient can be disposed both internally with distal portion 118 and externally upon a surface of distal portion 118. In some embodiments, even a portion of the active ingredient can be disposed externally upon the surface of distal portion 118 and be adhered more robustly and uniformly to microneedles 112 than is achieved by coating approaches due to the intimate mixing between the degradable polymer and the active ingredient in the first fluid. In some embodiments, the first fluid or a plurality of first fluids (e.g., first, second, third, or more fluids) can be introduced into mold 120 to introduce a concentration gradient of the active ingredient, dissolution or degradation gradient, or other chemical or mechanical properties in distal portion 118.

The microneedle array molds employed in fabricating some embodiments of the microneedle arrays disclosed herein can have any variety of sizes, shapes, well depths or dimensions, or composition. In some embodiments, the mold can be a silicone mold, which can facilitate the release of the microneedle arrays following their fabrication. Other materials can also facilitate the release of microneedle arrays from a microneedle array mold and can suitably be employed in the disclosure herein. For example, in some embodiments, a microneedle array mold can be silicone-coated or polytetrafluoroethylene-coated to facilitate release of a microneedle array from the mold.

In general, microneedle array molds can contain elongate wells of desired dimensions and number to promote formation of a microneedle array having desired properties. In addition, the microneedle array molds include an area for containing the second fluid upon overfilling the elongate wells. For example, in some embodiments, a lip can be present around the microneedle array mold to contain or permit pooling of the overfilled quantity of the second fluid as a continuous layer above the elongate wells. As discussed herein, an overfilled quantity or portion of the second fluid within the microneedle array mold can be converted into the base layer upon forming the microneedle arrays.

Any suitable technique can be used for introducing the first fluid and the second fluid into the elongate wells of the microneedle array molds. Since certain dissolvable polymers, particularly hyaluronic acid or crosslinked hyaluronic acid, can impart significant viscosity to the first fluid and/or the second fluid, it can sometimes be difficult to introduce the first fluid and/or the second fluid into the elongate wells within the microneedle array molds. Accordingly, in some embodiments of the methods disclosed herein, a casting process can be applied to the first fluid, the second fluid or both when they are in contact with the microneedle array mold. In illustrative embodiments, the casting process can utilize a vibrational mechanism or a cast mechanism to promote deeper fluid penetration into the elongate wells within the microneedle array mold.

For example, in some embodiments, the first fluid can be in the form of a viscous paste, and the second fluid can be in a less viscous form, such as a solution. The viscous paste first fluid can be applied to the surface of the microneedle array mold and then spread so that the viscous paste contacts each of the elongate wells. A first casting process can then be applied to promote penetration of the first fluid into the elongate wells of the microneedle array mold.

In the case of lower viscosity first or second fluids, the casting process can utilize centrifugal force or a similar technique to force the first fluid or the second fluid deeper into the elongate wells within the microneedle array mold. Other types of casting processes can also be utilized similarly to promote full penetration of the fluid(s) into the mold.

After introducing the first and second fluids into the microneedle array mold, the first and second fluids can be heated, dried, and/or evaporated at room temperature to drive off solvent therefrom and result in consolidation of the first polymer and the second polymer within the mold to form the microneedle array. Techniques for heating the mold can include, for example, direct radiant heating, resistive heating, heated air circulation, microwave heating, other suitable techniques, or any combination thereof.

The microneedle arrays of the present disclosure can be used in various treatment methods. In general, the treatment methods can comprise applying a microneedle array of the present disclosure to a skin surface of a subject to embed the plurality of microneedles in the skin surface. Upon becoming embedded in the skin surface, the microneedles can penetrate the epidermis and enter the dermis. The microneedle array can remain applied to the skin surface for a sufficient length of time for at least a portion of the active ingredient to be released from the microneedles into the dermis.

In some embodiments, the microneedle array can remain applied to the skin surface until sufficient dissolvable polymer dissolves to affect release of the microneedles from the base layer, thus leaving the microneedles behind in the dermis following removal of the base layer from the skin surface. If they are not already completely degraded by the time the microneedle array is removed from the skin surface, the microneedles can break from the base layer at a point of weakness along the microneedle and remain in the skin degrade over time to release their active material to the subject.

Conditions that can be treated with the microneedle arrays of the present disclosure include, but are not limited to, forehead lines, crow's feet, frown lines, finelines, hyperhidrosis, scarring, psoriasis, inflammatory dermatosis, and the like.

Figure 4:
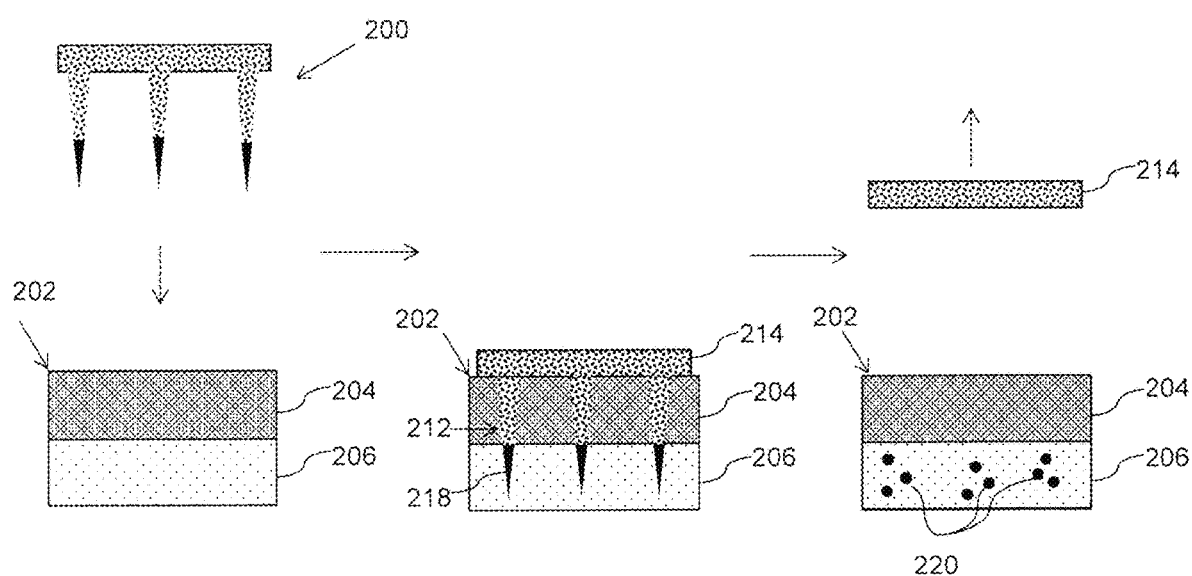
FIG. 4 shows an illustrative schematic demonstrating how a microneedle array of the present disclosure is used to treat a subject, according to some embodiments.

For example, FIG. 4 shows an illustrative schematic demonstrating how a microneedle array of the present disclosure is used to treat a subject. As shown, a microneedle array 200 can be applied to skin surface 202 of a subject. The skin surface 202 includes epidermis 204 and dermis 206. Upon being applied to the skin surface 202, the microneedles 212 penetrate the epidermis 204, and the distal portion 218 of each of the microneedles 212 at least partially enters the dermis 206. In the configuration shown in FIG. 4, the distal portion 218 of each microneedle 212 fully enters the dermis 206. At this juncture, the microneedle array 200 is allowed to remain in place on the skin surface 202 for at least a sufficient length of time for the microneedles 212 to begin dissolution and/or separate from the base layer 214. As depicted in FIG. 4, the microneedles 212 can completely dissolve at and/or within the skin surface 202, dermis 206, or epidermis 204 before removal of base layer 214 therefrom. However, full degradation or dissolution of the polymers is not required. Upon degradation of microneedles 212, active ingredient 220 is released into dermis 206 for performing a therapeutic function.

EXAMPLES

Example 1

A highly viscous fluid of hyaluronic acid was prepared by hydrating a dry hyaluronic acid fiber having a molecular weight of 500 kDa with phosphate buffered saline. The viscous fluid was transferred to a 1 mL syringe and centrifuged for 10 minutes at 4000 rpm to remove air bubbles. No active ingredient was employed in this example.

After removing air bubbles, 0.20 g of the viscous fluid was placed on a negative silicone microneedle mold. The applied fluid was cast to a thin film. After casting the fluid, the wet film and the mold were placed in an oven and heated at 40° C. for 2.5 hours. Following heating, a freestanding microneedle array was removed from the mold using a pair of tweezers. The thickness of the base layer was adjusted by casting different quantities of the viscous fluid onto the mold.

Figure 5:
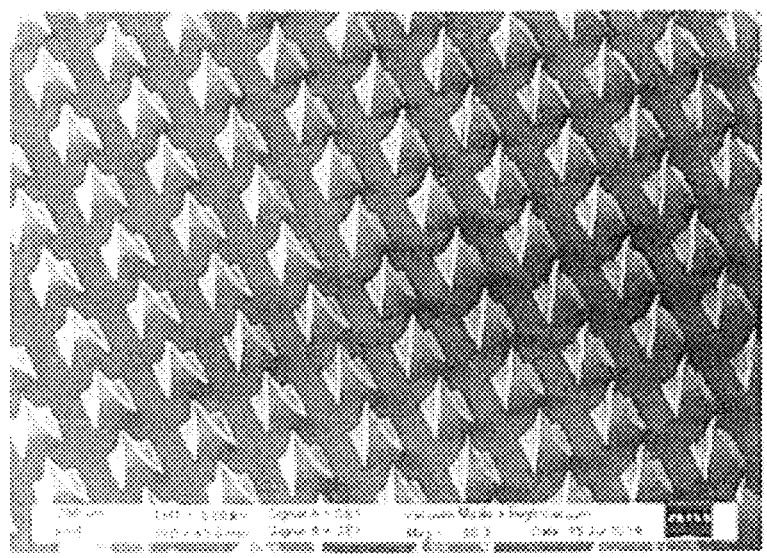
FIG. 5 shows a scanning electron microscope (SEM) image of a microneedle array, according to some embodiments.
Figure 6:
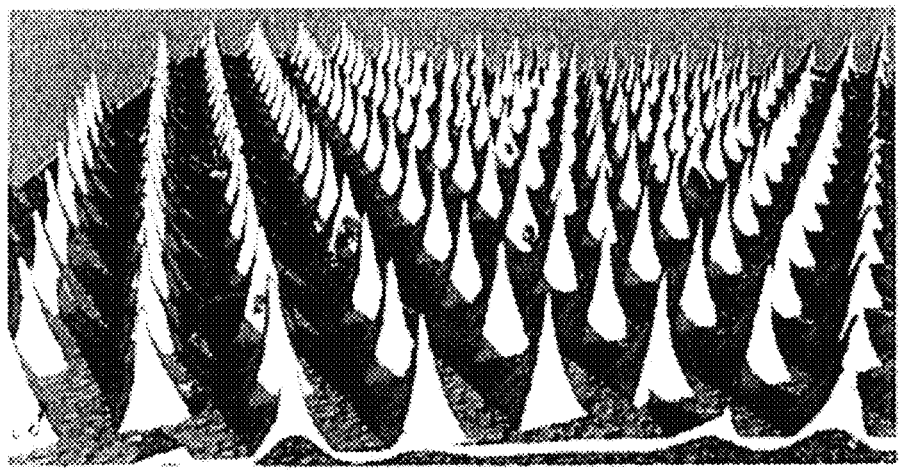
FIG. 6 shows an x-ray micro computerized tomography (CT) image of a microneedle array, according to some embodiments.

FIGS. 5 and 6 illustrate images of typical microneedles arrays produced using some embodiments of the manufacturing methods herein, including that discussed above with respect to Example 1. FIG. 5 shows a scanning electron microscope (SEM) image of the microneedle array, and FIG.

6 shows an x-ray micro computerized tomography (CT) image of the microneedle array.

Example 2

A microneedle array was prepared in a similar manner to Example 1, except a crosslinked hyaluronic acid was used in place of hyaluronic acid. Specifically, Juvederm Ultra Plus gel was lyophilized and reconstituted to a thick fluid having a hyaluronic acid concentration of 120 mg/mL. A mixture of hyaluronic acid and collagen or hyaluronic acid and fibroins was used similarly. No active ingredient was employed in this example.

Example 3

A microneedle array was prepared in a similar manner to Example 1, except a hydrophobically modified hyaluronic acid was used. Specifically, benzylated hyaluronic acid having a degree of benzylation of 80% was mixed with dimethyl sulfoxide to form a viscous paste containing 20 wt. % hyaluronic acid. In this case, drying took place in the oven for 24 hours at 45° C. No active ingredient was employed in this example.

Example 4

In this example, trypan blue (MW=873) was used as a model active ingredient for formulation with hyaluronic acid in forming a microneedle array. Trypan blue and hyaluronic acid were dissolved in PBS to form a viscous paste. The viscous paste was then cast in the silicone mold. After casting the trypan blue/hyaluronic acid into the mold, a similar paste also containing hyaluronic acid but lacking the trypan blue was cast on top of the originally placed paste in the mold. Heating was subsequently conducted for 2.5 hours at 45° C.

Figure 7:
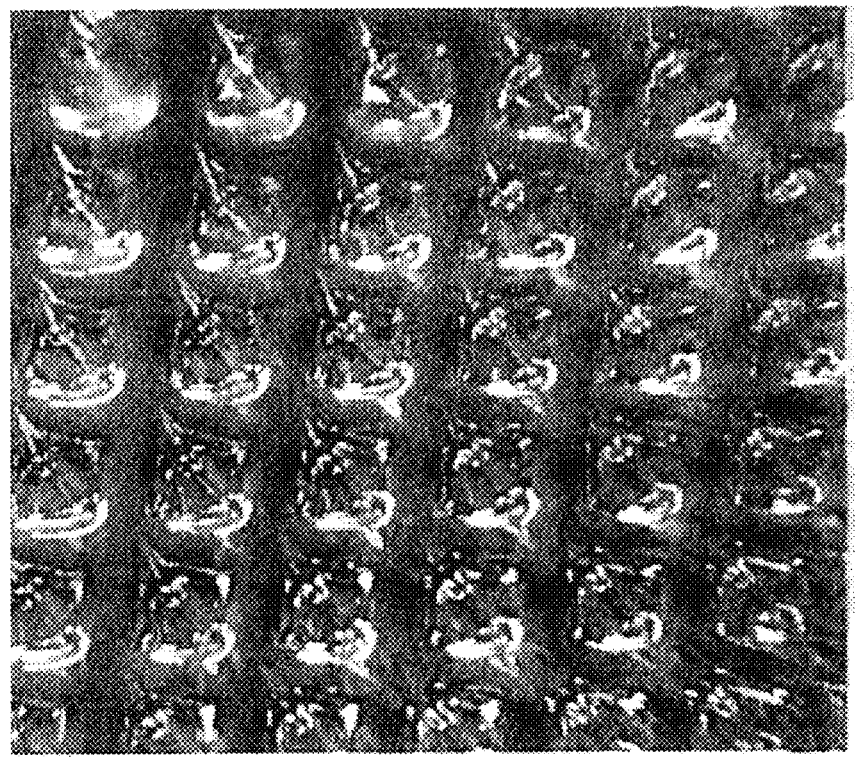
FIG. 7 shows an image of a microneedle array incorporating trypan blue within a distal portion of the microneedles, according to some embodiments.

A microneedle array having the trypan blue loaded preferentially within the distal portions of the microneedles resulted. FIG. 7 shows an image of a microneedle array having preferential loading of trypan blue within the distal portions of the microneedles.

Example 5

A microneedle array substituting fluorescein isothiocyanate (FITC)/human serum albumin (HSA) for trypan blue was formed in a similar manner to that of Example 4.

Example 6

A microneedle array substituting botulinium toxin type A (BoNT/A) for trypan blue was also formed in a similar manner to that of Example 4.

Example 7

Figure 8:
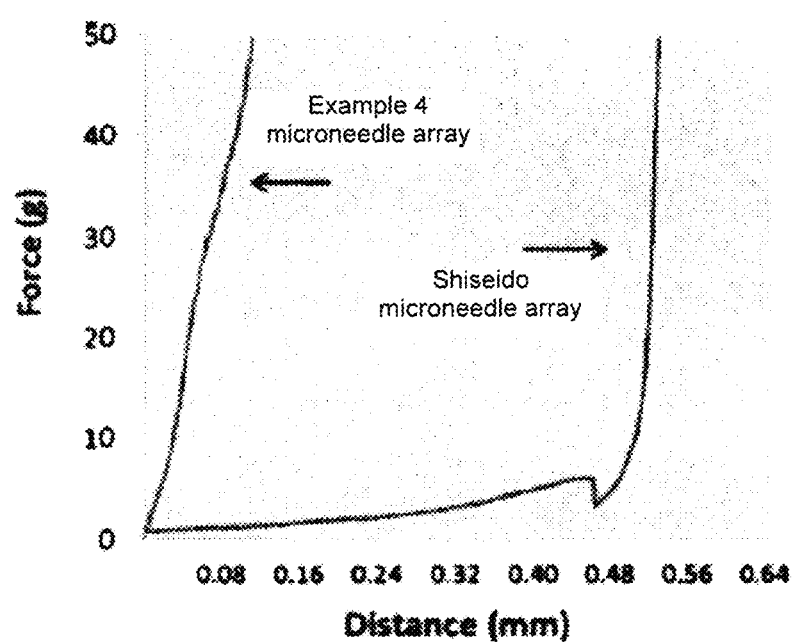
FIG. 8 shows a plot of force response versus probe travelling distance for a hyaluronic acid microneedle array in an embodiment disclosed herein in comparison to a commercially available microneedle array obtained from Shiseido, according to some embodiments.
Figure 9A:
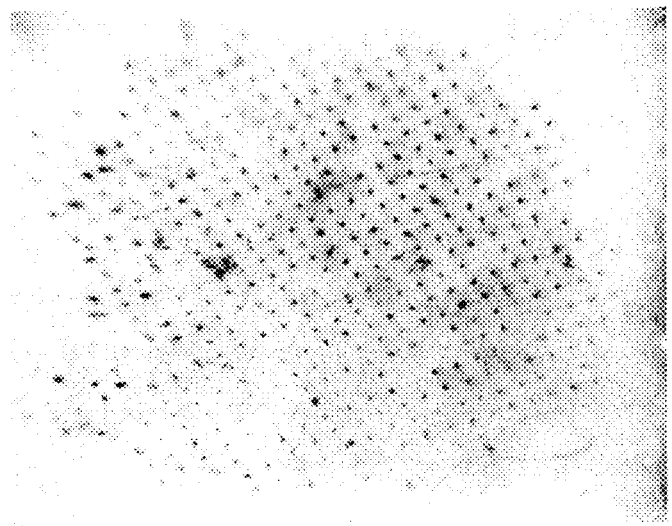
FIG. 9A shows a photograph of a skin sample treated with a dye-labeled microneedle array described herein, according to some embodiments.
Figure 9B:
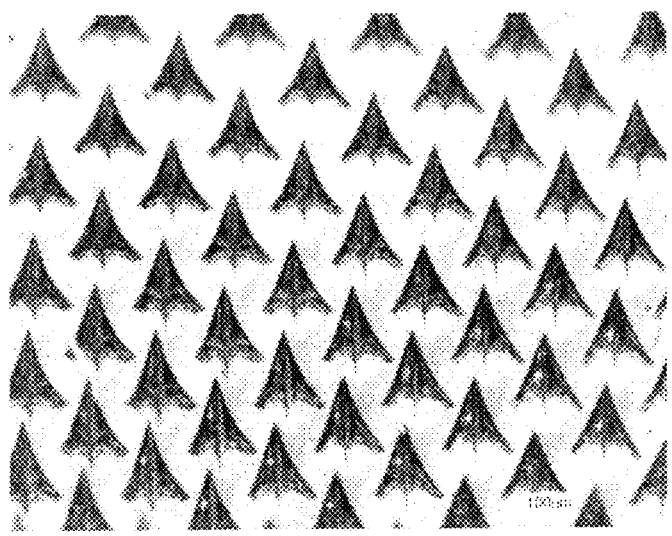
FIG. 9B shows a micrograph of an exemplary microneedle array taken prior to penetration of a skin sample, according to some embodiments.
Figure 9C:
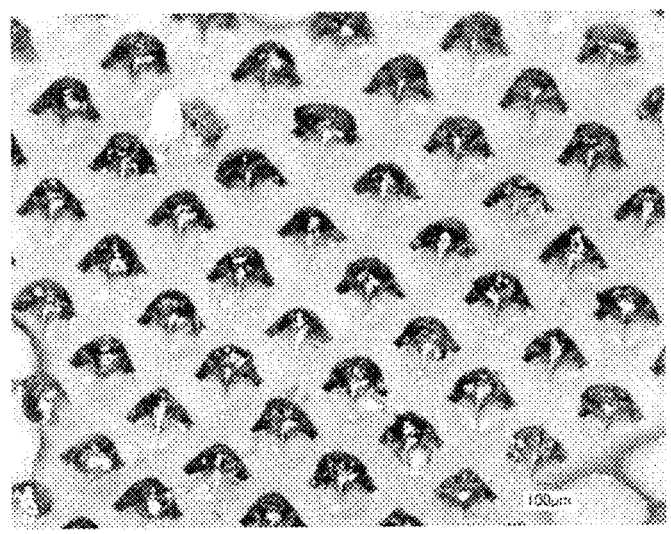
FIG. 9C shows a micrograph of the microneedle array of FIG. 9B taken after 5 minutes of penetration of a skin sample, according to some embodiments.

The mechanical properties of the microneedle array of Example 1 were measured using a Stable Microsystem texture analyzer. In performing these measurements, the microneedle array was place on a measuring surface with the microneedles facing upward. The probe from the texture analyzer was contacted with the microneedles and moved axially with respect to the microneedles. The force response as a function of the probe travelling distance was then recorded. FIG. 8 shows a plot of force response versus probe travelling distance for the hyaluronic acid microneedle array in comparison to a commercially available microneedle array obtained from Shiseido. As shown in FIG. 8, the hyaluronic acid microneedle array had a much higher mechanical strength.

Example 8

Skin perforation tests were conducted using human cadaver skin and the microneedle array of Example 5. The microneedle array was placed on the skin with the microneedles facing downward, and pressure was manually applied with a 2 kg weight for approximately one minute. A 190 g weight was then placed on an applicator on the microneedle array, and the weight was held in place for 60 minutes. The weight and applicator were then removed by pulling outward with respect to the skin. Confocal image analyses of the microneedles remaining in the skin were then conducted. The confocal image analyses showed penetration to a depth of about 100 µm within the skin, which may be suitable for some superficial applications.

Skin permeation studies were also conducted using a Franz-Cell Assay. The skin penetration studies were performed using an immunoglobulin G (IgG) loaded hyaluronic microneedle patch prepared in a manner similar to those described in Examples 1-6. The patch contained 2.8 (±0.24) µg IgG/patch.

A Franz cell (Logan Instruments) was pretreated with 5 mL of 5% bovine serum albumin (BSA) vehicle in PBS overnight with magnetic stirring at room temperature. The following day, the 5 mL vehicle was replaced with 5 mL of 1% BSA in PBS containing 1× proteinase inhibitor and prewarmed to 32° C. Human cadaver skin was thawed with room temperature water for 1 hour, cut into pieces to fit one microneedle patch, and then fastened onto a plastic foam with pins. The skin was stretched to make a tight, flat surface and wiped to remove the water on the skin. The patch was applied to the skin using an applicator for 1 minute, and then a weight of 300 g was placed on the patch and left for 4 minutes (5 minute study). A second skin sample was likewise was left for 30 minutes. The skin samples were applied onto the Franz cells with the stratum corneum layer facing upwards. The 1% BSA vehicle was then allowed to diffuse through the sample and 0.4 mL aliquots were taken from the receptor arm of the Franz cell and selected intervals. Each time an aliquot was taken 0.4 mL fresh 1% BSA vehicle containing 1× proteinase inhibitor was added to the cell.

Figure 10:
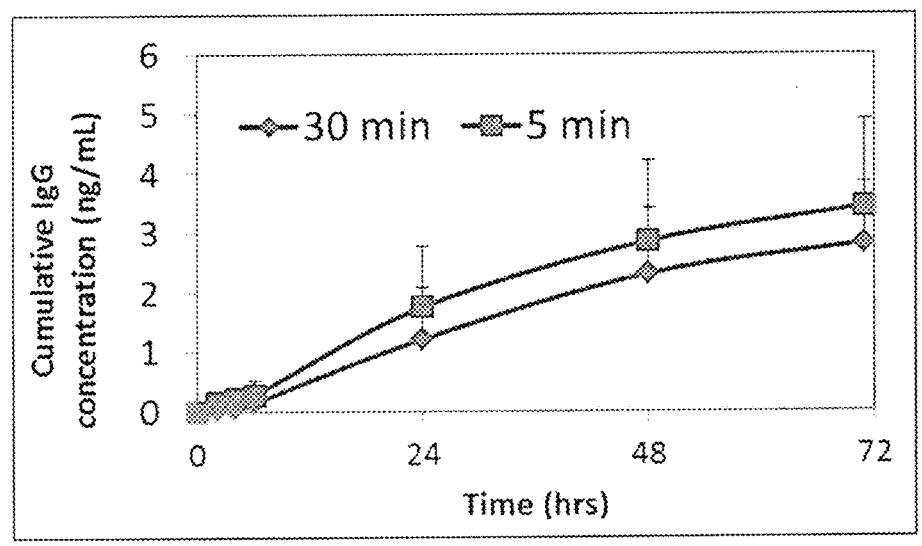
FIG. 10 shows the results of a study involving immunoglobulin G (IgG) dermal permeation through human cadaver skin, according to some embodiments.

The collected aliquots were then collected and studied using enzyme-linked immunosorbent assay (ELISA). To recover residual IgG from the skin samples, each skin sample was weighed and cut into small pieces. The pieces were incubated at 4° C. for at least 4 hours in a suspension of 50 mg skin per mL of 1% BSA (in PBS) containing 1× proteinase inhibitor. The tissues were then homogenized and rotated with a rocker at 5° C. overnight and subsequently centrifuged at 4700×g and 5° C. for 15 minutes to collect the supernatant. The supernatant was then analyzed using ELISA. The time dependent results of IgG permeation through the skin samples is provided in FIG. 10. This About 14-17 ng of IgG permeated through human cadaver skin after 70 hrs.

Example 11

A Toxin (900 kDa)-loaded HA microneedle patch was prepared using BoNT/A (900 kDa) having a concentration of 0.46 mg/ml (potency 4.70 E+7 (u/mg)); 160 kDa hyaluronic acid; and a buffer of 20 mM histidine of pH 6.0. 36 µL of toxin solution were added to 100 ml of 20 mM histidine buffer. The concentration after dilution was 0.000166 µg/µl. HA-toxin gel (12 wt %) was then prepared by adding 109 mg HA fiber (160 KDa) to a 5 ml Norm-Ject HSW syringe. 803.14 mg of toxin solution were added to a second 5 ml Norm-Ject HSW syringe. The two syringes were then connected using a female-to-female syringe connector, and the toxin solution was gently injected into the syringe with the HA fiber. The mixture was mixed back and forth for 10 cycles, and this mixing was repeated every five minutes for a total of 7 times. A second gel was prepared for to make a backing layer (base). 400 mg of 160 KDa HA was mixed with 1000 mg of pH 6.0 20 mM histidine buffer. The final HA concentration was 28.57 wt %.

Toxin-loaded microneedle array patches were then prepared. 18.2 mg of HA-toxin gel (12 wt % HA; toxin conc. 0.1458 ng/mg) were weighed onto a silicone microneedle mold. 125 mg of HA gel (28.57 wt % HA in 20 mM histidine buffer) was separately weighed out and pressed to a wet paste using to Teflon-sheets. The HA-paste was then cast onto the Ha-toxin solution which was on the silicone microneedle mold. A second Toxin (150 KDa)-loaded HA microneedle patch was prepared similar to procedure as described as above. The Toxin (900 kDa)-loaded HA microneedle and toxin (150 KDa)-loaded microneedle patch were further analyzed by mass recovery, cell-based potency assay (CBPA), and light chain (LC) activity assay.

Mass recovery was determined using ELISA assay with F12-3-8 monoclonal antibodies as the capture antibody, polyclonal detection antibody as the detection antibody. A total of five patches were analyzed, and toxin mass recovery was found to be 80 (±11.9) %.

CBPA studies were also performed to assess the potency of the 150/900 kDa BoNT/A complex in the microneedle arrays described herein.

Differentiation: The neuroblastoma cells were cultured for approximately 72 hours in the presence of trisialoganglioside and neuronal supplements to increase sensitivity of the cells to neurotoxin uptake.

Drug Treatment: The cells were incubated with the drug for 24 hours during which time the neurotoxin would bind to the cell surface receptor, was internalized, and the light chain endopeptidase domain was translocated into the cytosol where it cleaved $SNAP25_{206}$ between amino acids 197 and 198.

Accumulation of cleaved $SNAP25_{197}$: The cells were incubated for another 72 hours to allow for $SNAP25_{197}$ accumulation.

Quantification of $SNAP25_{197}$ by ElectroChemiluminescence (ECL)-ELISA: Cell lysates were collected and $SNAP25_{197}$ quantified with the SNAP25 ECL-ELISA. The ECL-ELISA signal for the reference standard, in relative light units, was plotted against the treatment concentration and the potency of the test sample is extrapolated from the standard curve equation.

In the above procedure the reference standard is Botox standard 016 (3 u/mL-0.0938 U/mL). The experimental control was a DS2 900 KDa drug substance lot used to make patches (2 U/mL). The results of this study showed the average recovery to be 69.3 (±5.96) %.

Evaluation of 900 kDa BoNT/A toxin loaded hyaluronic acid patches was also made using the Light-Chain Activity High-Performance Liquid Chromatography (LCA-HPLC) assay. These studies were performed to determine the recovery of 900 kDa BoNT/A toxin from dissolved hyaluronic acid patches using a the light chain activity HPLC assay described below.

Four patches were evaluated. Each patch was placed in a 5 mL Eppendorf Protein LoBind tube. Four mL volumes of Digestion Buffer (0.5 mM Zinc Acetate, 0.05% Tween 20, 2 mM DTT in 50 mM HEPES, pH 7.4) were added to each tube. Patches were dissolved at ambient room temperature for 1.5 hours. Tubes were placed on a shaker (200 rpm) throughout the 1.5 hour time period. Triplicate 350 µL volumes from each patch dissolution tube were transferred to 0.6 mL Axygen tubes for testing.

Standard curve concentrations of 0.05, 0.1, 0.5 and 1 ng/mL were prepared using the same material of 900 kDa BoNT/A toxin that was used to prepare the HA patches. The standard curve was prepared in Digestion Buffer. Triplicate 350 µL volumes of each standard curve concentration were transferred to 0.6 mL Axygen tubes for testing.

Samples were incubated for 30 minutes at 37° C. to facilitate sample reduction. Fifty µL, volumes of SNAPtide substrate were added to each sample tube. Sample tubes were incubated at ambient room temperature for 72 hours to allow for substrate cleavage. After 72 hours, 25 µL volumes of 5% trifuoracetic acid (TFA) were added to each sample tube to stop substrate cleavage. The contents of each tube were then transferred to HPLC vials for analysis. The fluorescently labeled cleavage product(s) were separated and detected via a RP-HPLC method using a Waters 2695 XE Separations Module (Waters Symmetry300 C18, 3.5 µm, 4.6×150 mm column) and a Waters 2475 Multi λ Fluorescence Detector. Data were collected and analyzed via Waters Empower Pro software. A standard curve was constructed by plotting the BoNT/A standard curve concentrations (x axis) versus the BoNT/A cleavage product peak areas (y axis). Patch concentrations were extrapolated from the curve. The concentration of BoNT/A contained in each patch was determined by multiplying the BoNT/A patch concentration by 4 (dilution factor).

The resultant test data are presented in Table 1. The average toxin recovery was 2.48±0.77 ng/patch. The average toxin patch potency equates to 116.6 units per patch.

TABLE 1

Summary of Light-Chain Activity High-Performance Liquid Chromatography (LCA-HPLC) Assay Results When Evaluating 900 kDa BoNT/A Toxin Loaded Patches

| | Average Peak Area | Standard Deviation | ng/mL | ng/patch |
|---|---|---|---|---|
| Patch 1 | 914368.3 | 32738.9 | 0.45 | 1.80 |
| Patch 2 | 1793514.7 | 16122.0 | 0.89 | 3.55 |
| Patch 3 | 1249298.0 | 42165.4 | 0.62 | 2.47 |
| Patch 4 | 1059296.3 | 167983.4 | 0.52 | 2.09 |

Further Considerations

In some embodiments, any of the clauses herein may depend from any one of the independent clauses or any one of the dependent clauses. In one aspect, any of the clauses (e.g., dependent or independent clauses) may be combined with any other one or more clauses (e.g., dependent or independent clauses). In one aspect, a claim may include some or all of the words (e.g., steps, operations, means or components) recited in a clause, a sentence, a phrase or a paragraph. In one aspect, a claim may include some or all of the words recited in one or more clauses, sentences, phrases or paragraphs. In one aspect, some of the words in each of the clauses, sentences, phrases or paragraphs may be removed. In one aspect, additional words or elements may be added to a clause, a sentence, a phrase or a paragraph. In one aspect, the subject technology may be implemented without utilizing some of the components, elements, functions or operations described herein. In one aspect, the subject technology may be implemented utilizing additional components, elements, functions or operations.

The subject technology is illustrated, for example, according to various aspects described below. Various examples of aspects of the subject technology are described as numbered clauses (1, 2, 3, etc.) for convenience. These are provided as examples and do not limit the subject technology. It is noted that any of the dependent clauses may be combined in any combination, and placed into a respective independent clause, e.g., clause 1 or clause 20. The other clauses can be presented in a similar manner.

Clause 1. A microneedle array comprising: a base layer; a plurality of microneedles projecting from the base layer, each of the microneedles comprising an elongate body having a proximal portion and a distal portion, the proximal portion being attached to the base layer, and each of the microneedles comprising at least one dissolvable polymer; and an active ingredient incorporated in the elongate body, the active ingredient being present only in the distal portion and at least internally in the distal portion.

Clause 2. The microneedle array of Clause 1, wherein the active ingredient comprises a neurotoxin.

Clause 3. The microneedle array of Clause 2, wherein the neurotoxin comprises a botulinum toxin.

Clause 4. The microneedle array of Clause 3, wherein the botulinium toxin is type A, B, C, D or E.

Clause 5. The microneedle array of Clause 3, wherein the botulinum toxin is selected from the group consisting of Botulinum toxin serotype A (BoNT/A), Botulinum toxin serotype B (BoNT/B), Botulinum toxin serotype C1 (BoNT/C1), Botulinum toxin serotype D (BoNT/D), Botulinum toxin serotype E (BoNT/E), Botulinum toxin serotype F (BoNT/F), Botulinum toxin serotype G (BoNT/G), Botulinum toxin serotype H (BoNT/H), Botulinum toxin serotype X (BoNT/X), and mosaic Botulinum toxins and/or variants thereof.

Clause 6. The microneedle array of any one of the preceding Clauses, wherein the at least one dissolvable polymer of each microneedle comprises a first dissolvable polymer, the distal portion and the proximal portion both comprising the first dissolvable polymer.

Clause 7. The microneedle array of Clause 6, wherein the base layer comprises the first dissolvable polymer.

Clause 8. The microneedle array of any one of Clauses 1-5, wherein the distal portion comprises a first dissolvable polymer and the proximal portion comprises a second dissolvable polymer, the first dissolvable polymer and the second dissolvable polymer differing from one another.

Clause 9. The microneedle array of Clause 8, wherein the base layer comprises the second dissolvable polymer.

Clause 10. The microneedle array of any of the preceding Clauses, wherein the proximal portion and the base layer lack any active ingredients.

Clause 11. The microneedle array of Clause 10, wherein the proximal portion and the base layer consist of the at least one dissolvable polymer.

Clause 12. The microneedle array of any one of the preceding Clauses, wherein each dissolvable polymer is independently selected from a polymeric material that dissolves in an phosphate buffered saline (PBS) having a pH in the range of about 6.8 to about 7.8 at a temperature in the range of about 10° C. to about 50° C.

Clause 13. The microneedle array of any one of the preceding Clauses, wherein the at least one dissolvable polymer comprises hyaluronic acid, crosslinked hyaluronic acid, hydrophobically modified hyaluronic acid, or any combination thereof.

Clause 14. The microneedle array of any one of the preceding Clauses, wherein the at least one dissolvable polymer comprises at least one of a glycosaminoglycan, a polysaccharide, collagen, elastin, fibroin, starch, glucomannan, hyaluronic acid, crosslinked hyaluronic acid, hydrophobically modified hyaluronic acid, or any combination thereof.

Clause 15. The microneedle array of any one of the preceding Clauses, wherein the active ingredient is dispersed in a matrix of the at least one dissolvable polymer in the distal portion.

Clause 16. The microneedle array of any one of the preceding Clauses, wherein each microneedle has a length ranging between about 25 microns and about 3000 microns.

Clause 17. The microneedle array of any one of the preceding Clauses, wherein each microneedle has substantially the same length.

Clause 18. The microneedle array of any one of the preceding Clauses, wherein each microneedle has a conical or pyramidal geometry.

Clause 19. The microneedle array of any one of the preceding Clauses, wherein each microneedle has a tip width ranging between about 1 microns to about 30 microns.

Clause 20. The microneedle array of any one of the preceding Clauses, wherein a density of microneedles within the microneedle array ranges between about 5 microneedles/$cm^2$ to about 1000 microneedles/$cm^2$.

Clause 21: The microneedle array of any one of the preceding Clauses, wherein the active ingredient is disposed uniformly in the distal portion.

Clause 22: The microneedle array of any one of the preceding Clauses, wherein the active ingredient is present in a gradient in the distal portion.

Clause 23. A method for forming a microneedle array, the method comprising: providing a microneedle array mold comprising a plurality of elongate wells, each of the elongate wells comprising a lower portion and an upper portion; filling the lower portion of each of the elongate wells with a first fluid comprising a first dissolvable polymer and an active ingredient, each of the elongate wells being only partially filled to leave the upper portion of each of the elongate wells unfilled; after filling the lower portion of each of the elongate wells, overfilling the unfilled upper portion of each of the elongate wells with a second fluid, the second fluid comprising a second dissolvable polymer and lacking the active ingredient; and heating the mold or drying the first and second fluids in the mold at room temperature to form a microneedle array comprising a base layer having a plurality of microneedles projecting therefrom.

Clause 24. The method of Clause 23, wherein a casting process is used to place at least one of the first fluid and the second fluid in each of the elongate wells.

Clause 25. The method of Clause 24, wherein filling the lower portion of each of the elongate wells comprises casting the first fluid into the lower portion of each of the elongate wells.

Clause 26. The method of Clause 25, wherein the overfilling the upper portion of each of the elongate wells comprises casting the second fluid into the upper portion of each of the elongate wells.

Clause 27. The method of Clause 24, wherein the overfilling the upper portion of each of the elongate wells comprises casting the first fluid and the second fluid into each of the elongate wells.

Clause 28. The method of any one of Clauses 23-27, wherein at least a portion of the second fluid is disposed in an overfilled or base portion of the mold, the second fluid disposed in the overfilled portion of the mold defining the base layer of the microneedle array.

Clause 29. The method of any one of Clauses 23-28, wherein the method further comprises separating the microneedle array from the microneedle array mold.

Clause 30. The method of any one of Clauses 23-29, wherein the first fluid has a higher viscosity than the second fluid.

Clause 31. The method of any one of Clauses 23-30, wherein a first casting process is utilized to deposit the first fluid in the microneedle array mold before overfilling the unfilled upper portion of each of the elongate wells with the second fluid.

Clause 32. The method of Clause 31, wherein a second casting process is utilized to deposit the second fluid on the first fluid in the microneedle array mold.

Clause 33. The method of any one of Clauses 23-32, wherein the active ingredient comprises a neurotoxin.

Clause 34. The method of Clause 33, wherein the neurotoxin comprises a botulinum toxin.

Clause 35. The method of Clause 34, wherein the botulinium toxin is type A, B, C, D or E.

Clause 36. The method of any one of Clauses 23-35, wherein the first dissolvable polymer and the second dissolvable polymer are the same.

Clause 37. The method of any one of Clauses 23-36, wherein the first dissolvable polymer and the second dissolvable polymer comprise at least one of hyaluronic acid, crosslinked hyaluronic acid, hydrophobically modified hyaluronic acid, or any combination thereof.

Clause 38. The method of any one of Clauses 23-37, wherein the first dissolvable polymer and the second dissolvable polymer comprise at least one of a glycosaminoglycan, a polysaccharide, collagen, elastin, fibroin, starch, glucomannan, hyaluronic acid, crosslinked hyaluronic acid, hydrophobically modified hyaluronic acid, or any combination thereof.

Clause 39. A method for treating a subject, the method comprising: providing a microneedle array comprising: a base layer; a plurality of microneedles projecting from the base layer, each of the microneedles comprising an elongate body having a proximal portion and a distal portion, the proximal portion being attached to the base layer, and each of the microneedles comprising at least one dissolvable polymer; and an active ingredient incorporated in the elongate body, the active ingredient being present only in the distal portion and at least internally in the distal portion; and applying the microneedle array to a skin surface of a subject to embed the plurality of microneedles in the skin surface.

Clause 40. The method of Clause 39, wherein the at least one dissolvable polymer dissolves while the plurality of microneedles are embedded in the skin surface to release the active ingredient to the subject.

Clause 41. The method of Clause 39 or 40, further comprising removing the base layer from the skin surface of the subject after the at least one dissolvable polymer dissolves.

Clause 42. The method of any one of Clauses 39-41, wherein the active ingredient comprises a neurotoxin.

Clause 43. The method of Clause 42, wherein the neurotoxin comprises a botulinum toxin.

Clause 44. The method of any one of Clauses 39-43, wherein the at least one dissolvable polymer of each of the microneedles comprises a first dissolvable polymer, the distal portion and the proximal portion both comprising the first dissolvable polymer Clause 45. The method of Clause 44, wherein the base layer comprises the first dissolvable polymer.

Clause 46. The method of any one of Clauses 39-45, wherein the at least one dissolvable polymer comprises hyaluronic acid, crosslinked hyaluronic acid, hydrophobically modified hyaluronic acid, or any combination thereof.

Clause 47. The method of any one of Clauses 39-45, wherein the at least one dissolvable polymer comprises at least one of a glycosaminoglycan, a polysaccharide, collagen, elastin, fibroin, starch, glucomannan, hyaluronic acid, crosslinked hyaluronic acid, hydrophobically modified hyaluronic acid, or any combination thereof.

Clause 48. The method of any one of Clauses 39-47, wherein the microneedle array is used to treat forehead lines, crow's feet, frown lines, fineline, hyperhidrosis, scarring, psoriasis, or inflammatory dermatosis.

The foregoing description is provided to enable a person skilled in the art to practice the various configurations described herein. While the subject technology has been particularly described with reference to the various figures and configurations, it should be understood that these are for illustration purposes only and should not be taken as limiting the scope of the subject technology.

There may be many other ways to implement the subject technology. Various functions and elements described herein may be partitioned differently from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

As used herein, the phrase "at least one of" preceding a series of items, with the term "and" or "or" to separate any of the items, modifies the list as a whole, rather than each member of the list (i.e., each item). The phrase "at least one of" does not require selection of at least one of each item listed; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

Terms such as "top," "bottom," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Furthermore, to the extent that the term "include," "have," or the like is used in the description or the claims, such term is intended to be inclusive in a manner similar to the term "comprise" as "comprise" is interpreted when employed as a transitional word in a claim.

The word "exemplary" is used herein to mean "serving as an example, instance, or illustration." Any embodiment described herein as "exemplary" is not necessarily to be construed as preferred or advantageous over some embodiments.

A reference to an element in the singular is not intended to mean "one and only one" unless specifically stated, but rather "one or more." Pronouns in the masculine (e.g., his) include the feminine and neuter gender (e.g., her and its) and vice versa. The term "some" refers to one or more. Underlined and/or italicized headings and subheadings are used for convenience only, do not limit the subject technology, and are not referred to in connection with the interpretation of the description of the subject technology. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

What is claimed is:

1. A microneedle array comprising:
a base layer;
a plurality of microneedles projecting from the base layer, each of the microneedles comprising:
an elongate body having a proximal portion and a distal portion,
the distal portion comprising a first dissolvable polymer and an active ingredient incorporated within a matrix of the first dissolvable polymer,
the proximal portion being contiguous with and attached to the base layer,
wherein the proximal portion and the base layer comprise the first dissolvable polymer and substantially no active ingredient.

2. The microneedle array of claim 1, wherein the active ingredient comprises a neurotoxin.

3. The microneedle array of claim 2, wherein the neurotoxin comprises a botulinum toxin.

4. The microneedle array of claim 3, wherein the botulinum toxin is selected from the group consisting of Botulinum toxin serotype A (BoNT/A), Botulinum toxin serotype B (BoNT/B), Botulinum toxin serotype C1 (BoNT/C1), Botulinum toxin serotype D (BoNT/D), Botulinum toxin serotype E (BoNT/E), Botulinum toxin serotype F (BoNT/F), Botulinum toxin serotype G (BoNT/G), Botulinum toxin serotype H (BoNT/H), Botulinum toxin serotype X (BoNT/X), and mosaic Botulinum toxins and/or variants thereof.

5. The microneedle array of claim 1, wherein the first dissolvable polymer comprises hyaluronic acid, crosslinked hyaluronic acid, hydrophobically modified hyaluronic acid, or any combination thereof.

6. The microneedle array of claim 1, wherein the first dissolvable polymer comprises at least one of a glycosaminoglycan, a polysaccharide, collagen, elastin, fibroin, starch, glucomannan, hyaluronic acid, crosslinked hyaluronic acid, hydrophobically modified hyaluronic acid, or any combination thereof.

7. A method comprising:
providing a microneedle array comprising:
a base layer;
a plurality of microneedles projecting from the base layer, each of the microneedles comprising an elongate body having a proximal portion and a distal portion, the distal portion comprising a first dissolvable polymer and an active ingredient incorporated within a matrix of the first dissolvable polymer, and the proximal portion being contiguous with and attached to the base layer,
wherein the proximal portion and the base layer have substantially no active ingredient; and
applying the microneedle array to a skin surface of a subject to embed the plurality of microneedles in the skin surface.

8. The method of claim 7, wherein the first dissolvable polymer dissolves while the plurality of microneedles are embedded in the skin surface to release the active ingredient to the subject.

9. The method of claim 8, further comprising removing the base layer from the skin surface of the subject after the first dissolvable polymer dissolves.

10. The method of claim 7, wherein the active ingredient comprises a neurotoxin.

11. The method of claim 10, wherein the neurotoxin comprises a botulinum toxin.

12. The method of claim 7, wherein the first dissolvable polymer comprises hyaluronic acid, crosslinked hyaluronic acid, hydrophobically modified hyaluronic acid, or any combination thereof.

13. The method of claim 7, wherein the first dissolvable polymer comprises at least one of a glycosaminoglycan, a polysaccharide, collagen, elastin, fibroin, starch, glucomannan, hyaluronic acid, crosslinked hyaluronic acid, hydrophobically modified hyaluronic acid, or any combination thereof.

14. The microneedle array of claim 1, wherein the distal portion comprises a first distal portion adjacent the proximal portion and a second distal portion longitudinally separated from the proximal portion by the first distal portion, and the first distal portion and the second distal portion have different active ingredient concentrations.

15. The microneedle array of claim 1, wherein the proximal portion has a length in a range from 1% to 99% of a length of the elongate body.

16. The microneedle array of claim 1, wherein the elongate body tapers longitudinally from the proximal portion to the distal portion, the distal portion terminating in a tip having a width in a range from 1 µm to 30 µm.

17. A microneedle array comprising:
a base layer comprising a first dissolvable polymer;
a plurality of microneedles projecting from the base layer, each of the microneedles comprising an elongate body having:
a proximal portion comprising the first dissolvable polymer and being attached to the base layer, and
a distal portion comprising a second dissolvable polymer and an active ingredient homogenously incorporated therewithin,
wherein the proximal portion and the base layer have substantially no active ingredient.

18. The microneedle array of claim 17, wherein the first dissolvable polymer and the second dissolvable polymer are the same.

19. The microneedle array of claim 17, wherein the first dissolvable polymer comprises hyaluronic acid, crosslinked hyaluronic acid, hydrophobically modified hyaluronic acid, or any combination thereof.

20. The microneedle array of claim 17, wherein the first dissolvable polymer comprises at least one of a glycosaminoglycan, a polysaccharide, collagen, elastin, fibroin, starch, glucomannan, hyaluronic acid, crosslinked hyaluronic acid, hydrophobically modified hyaluronic acid, or any combination thereof.

21. The microneedle array of claim 17, wherein the active ingredient comprises a neurotoxin.

22. The microneedle array of claim 21, wherein the neurotoxin comprises a botulinum toxin.

23. The microneedle array of claim 22, wherein the botulinum toxin is selected from the group consisting of Botulinum toxin serotype A (BoNT/A), Botulinum toxin serotype B (BoNT/B), Botulinum toxin serotype C1 (BoNT/C1), Botulinum toxin serotype D (BoNT/D), Botulinum toxin serotype E (BoNT/E), Botulinum toxin serotype F (BoNT/F), Botulinum toxin serotype G (BoNT/G), Botulinum toxin serotype H (BoNT/H), Botulinum toxin serotype X (BoNT/X), and mosaic Botulinum toxins and/or variants thereof.

24. The microneedle array of claim 17, wherein the distal portion comprises a first distal portion adjacent the proximal portion and a second distal portion longitudinally separated from the proximal portion by the first distal portion, and
wherein the first distal portion comprises a first amount of the active ingredient homogeneously incorporated therewithin and the second distal portion comprises a second amount of the active ingredient homogeneously incorporated therewithin.

25. The microneedle array of claim 17, wherein the proximal portion has a length in a range from 1% to 99% of a length of the elongate body.

26. The microneedle array of claim 17, wherein the elongate body tapers longitudinally from the proximal portion to the distal portion, the distal portion terminating in a tip having a width in a range from 1 µm to 30 µm.

* * * * *